(12) United States Patent
DeHoff et al.

(10) Patent No.: US 9,309,523 B2
(45) Date of Patent: Apr. 12, 2016

(54) NANNOCHLOROPSIS KOZAK CONSENSUS SEQUENCE

(71) Applicants: Peter DeHoff, Poway, CA (US); Leah Soriaga, San Diego, CA (US)

(72) Inventors: Peter DeHoff, Poway, CA (US); Leah Soriaga, San Diego, CA (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 431 days.

(21) Appl. No.: 13/705,284

(22) Filed: Dec. 5, 2012

(65) Prior Publication Data

US 2014/0154740 A1 Jun. 5, 2014

(51) Int. Cl.
*C07H 21/04* (2006.01)
*C12N 15/79* (2006.01)
*C12N 15/82* (2006.01)

(52) U.S. Cl.
CPC ............ *C12N 15/79* (2013.01); *C12N 15/8216* (2013.01)

(58) Field of Classification Search
None
See application file for complete search history.

(56) References Cited

U.S. PATENT DOCUMENTS

| | | | |
|---|---|---|---|
| 5,661,017 A | 8/1997 | Dunahay et al. | 435/172.3 |
| 7,449,568 B2 | 11/2008 | Fukuda et al. | 536/24.1 |
| 2008/0155705 A1 | 6/2008 | Zank et al. | 800/13 |
| 2009/0317904 A1 | 12/2009 | Vick et al. | 435/320.1 |
| 2010/0196913 A1 | 8/2010 | Hartner et al. | 435/6 |
| 2010/0210832 A1 | 8/2010 | Kilian et al. | 526/24.1 |
| 2010/0306880 A1 | 12/2010 | Briggs et al. | 800/296 |
| 2011/0014708 A1 | 1/2011 | Tsai et al. | 435/471 |

FOREIGN PATENT DOCUMENTS

| | | |
|---|---|---|
| WO | WO 00/62601 | 10/2000 |
| WO | WO 2007/133558 | 11/2007 |
| WO | WO 2011/034863 | 3/2011 |

OTHER PUBLICATIONS

Bruchez, J., et al. (1993), Regulatory sequences in the transcription of *Neurospora crassa* genes: CAAT box, TATA box, Introns, Poly(A) tail formation sequences, *Minireview*, 40: 89-96.
Gibson, D., et al. (2009), "Enzymatic assembly of DNA molecules up to several hundred kilobases", *Nature Methods*, 6(5): 343-345.
Hallmann, A., et al. (1997), "Gene replacement by homologous recombination in the multicellular green alga *Volvox carteri*", *Proc. Natl. Acad. Sci USA*, 94:7469-7474.
Hamilton, R., et al. (1987), "Compilation and comparison of the sequence context around the AUG startcodons in *Saccharomyces cerevisiae* mRNAs", *Nucleic Acids Research*, 15: 3581-3593.

Hellen, C., et al. (2001), "Internal ribosome entry sites in eukaryotic mRNA molecules", *Genes & Development*, 15:1593-1612.
Henikoff, S., et al. (1992), "Amino acid substitution matrices from protein blocks", *Proc. Natl. Acad. Sci USA*, 89:10915-10919.
Ikeda, K., et al. (1998), "Compilation of mRNA sequences surrounding the AUG translation initiation codon in the green alga *Chlamydomonas reinhardtii*" *Biosci. Biotechnol. Biochem.*, 62(12): 2457-2459.
Iwai, M., et al. (2004), "Improved genetic transformation of the thermophilic cyanobacterium, *Thermosynechoccus elongates* BP-1", *Plant Cell Physiol*. 45(2):171-175.
Joshi, C., et al. (1997), "Context sequences of translation initiation codon in plants", *Plant Molecular Biology*, 35: 993-1001.
Kim, J., et al. (2011), "High cleavage efficiency of a 2A peptide derived from porcine teschovirus-1 in human cell lines, zebrafish and mice" *PloS One*, 6(4): e18556.
Kindle, K., et al. (1989), "Stable nuclear transformation of *Chlamydomonas* using the *Chlamydomonas* gene for nitrate reductase", *The Journal of Cell Biology*, 109 (6, Part 1), 2589-2601.
Kindle, K. (1990), "High-frequency nuclear transformation of *Chlamydomonas reinhardtii*", *Proc. Natl. Acad. Sci. USA*, 87: 1228-1232.
Komar, A., et al. (2011), "Cellular IRES-mediated translation", *Cell Cycle*, 10(2): 229-240.
Kozak, M. (1986), "Point mutations define a sequence flanking the AUG initiator codon that modulates translation by eukaryotic ribosomes", *Cell*. vol. 44: 283-292.
Kozak, M. (1987), "An analysis of 5'-noncoding sequences from 699 vertebrate messenger RNA's", *Nucleic Acids Research*, 15(20): 8125-8148.
Lütcke, H.A., et al. (1987), "Selection of AUG initiation codons differs in plants and animals", *The EMBO Journal*, 6(1): 43-48.
Méndez-Alvarez, S., et al. (1994), "Transformation of *Chlorobium limicola* by a plasmid that confers the ability to utilize thiosulfate" *Journal of Bacteriology*,176(23):7395-7397.
Mortazavi, A., et al. (2008), "Mapping and quantifying mammalian transcriptomes by RNA-Seq", *Nature Methods*, 5(7): 621-628.
Ohnuma M., et al. (2008), "Polyethylene glycol (PEG)-mediated transient gene expression in a red alga, *Cyanidioschyzon merolae* 10D", *Plant Cell Physiol*. 49(1):117-120.
Pearson, W., et al. (1988), "Improved tools for biological sequence comparison", *Proc. Natl. Acad. Sci USA*, 85: 2444-2448.
Perrone, C., et al. (1998), "The *Chlamydomonas IDA7* locus encodes a 140 kDa dynein intermediate chain required to assemble the I1 inner arm complex", *Molecular Biology of the Cell*, 9:3351-3365.
Ravindran, C., et al. (2006), "Electroporation as a tool to transfer the plasmid pRL489 in *Oscillatoria* MKU 277" *Journal of Microbiological Methods*, 66:174-176.
Smith, T., et al. (1981), "Comparison of biosequences", *Advances in Applied Mathematics*, 2: 482-489.

(Continued)

*Primary Examiner* — Michele K Joike
(74) *Attorney, Agent, or Firm* — Harness, Dickey & Pierce, P.L.C.

(57) ABSTRACT

The present invention provides *Nannochloropsis* consensus Kozak sequences for use in protein expression in eukaryotic cells, such as algal cells. The invention further provides expression constructs, expression cassettes, cloning or expression vectors and host eukaryotic cells, such as algal cells, and methods for expressing proteins of interest which take advantage of the consensus Kozak sequences as described herein.

23 Claims, 2 Drawing Sheets

(56) References Cited

OTHER PUBLICATIONS

Steinbrenner, J., et al. (2006), "Transformation of the Green Alga *Haematococcus pluvialis* with a phytoene Desaturase for accelerated astaxanthin biosynthesis" *Applied and Environmental Microbiology* 72(12):7477-7484.

Sun, Y., et al. (2006), "Functional complementation of a nitrate reductase defective mutant of a green alga *Dunaliella viridis* by introducing the nitrate reductase gene", *Gene* 377:140-149.

Tan, C., et al. (2005), "Establishment of a micro-particle bombardment transformation system for *Dunaliella saline*", *The Journal of Microbiology* 43(4):361-365.

Wijffels, R., et al. (2010), "An outlook on microalgal biofuels", *Science Magazine*, 329(5993): 796-799.

Hinnebusch, A.G. (2011) "Molecular mechanism of scanning and start codon selection in eukaryotes", *Microbiology and Molecular Biology Reviews*, 75(3):434-467.

Kozak, M. (1999) "Initiation of translation in prokaryotes and eukaryotes", *Gene*, 234:187-208.

Valášek, L.S. (2012) "'Ribozoomin'—Translation initiation from the perspective of the ribosome-bound eukaryotic initiation factors (eIFs)", *Current Protein and Peptide Science*, 13:305-330.

Li, S., et al. (2009), "Transgenic microalgae as a non-antibiotic bactericide producer to defend against bacterial pathogen infection in the fish digestive tract", *Fish & Shellfish Immunology*, 26: 316-325.

Schroda, M., et al. (2000), "The HSP70A promoter as a tool for the improved expression of transgenes in *Chlamydomonas*", *The Plant Journal*, 21(2): 121-131.

International Search Report and Written Opinion dated May 8, 2013 issued in PCT Application No. PCT/US2012/067851.

International Preliminary Report on Patentability dated Jun. 18, 2015 issued in PCT Patent Application No. PCT/US2012/067851.

SEQUENCE LISTING

<160> NUMBER OF SEQ ID NOS: 20

<210> SEQ ID NO 1
<211> LENGTH: 12
<212> TYPE: DNA
<213> ORGANISM: Nannochloropsis gaditana

<400> SEQUENCE: 1
gcaaccatgg ct                                                          12

<210> SEQ ID NO 2
<211> LENGTH: 12
<212> TYPE: DNA
<213> ORGANISM: Nannochloropsis gaditana

<400> SEQUENCE: 2
gcaatcatgg ct                                                          12

<210> SEQ ID NO 3
<211> LENGTH: 12
<212> TYPE: DNA
<213> ORGANISM: Nannochloropsis gaditana

```
<400> SEQUENCE: 3
gcaaccatgg cg                                                          12

<210> SEQ ID NO 4
<211> LENGTH: 12
<212> TYPE: DNA
<213> ORGANISM: Nannochloropsis gaditana

<400> SEQUENCE: 4
gcaatcatgg cg                                                          12

<210> SEQ ID NO 5
<211> LENGTH: 12
<212> TYPE: DNA
<213> ORGANISM: Nannochloropsis gaditana

<400> SEQUENCE: 5
tcaaccatgg ct                                                          12

<210> SEQ ID NO 6
<211> LENGTH: 12
<212> TYPE: DNA
<213> ORGANISM: Nannochloropsis gaditana

<400> SEQUENCE: 6
tcaatcatgg ct                                                          12

<210> SEQ ID NO 7
<211> LENGTH: 12
<212> TYPE: DNA
<213> ORGANISM: Nannochloropsis gaditana

<400> SEQUENCE: 7
tcaaccatgg cg                                                          12

<210> SEQ ID NO 8
<211> LENGTH: 12
<212> TYPE: DNA
<213> ORGANISM: Nannochloropsis gaditana

<400> SEQUENCE: 8
tcaatcatgg cg                                                          12

<210> SEQ ID NO 9
<211> LENGTH: 12
<212> TYPE: DNA
<213> ORGANISM: Nannochloropsis gaditana

<400> SEQUENCE: 9
gcaaacatgg ct                                                          12

<210> SEQ ID NO 10
<211> LENGTH: 12
<212> TYPE: DNA
<213> ORGANISM: Nannochloropsis gaditana

<400> SEQUENCE: 10
gcaaacatgg cg                                                          12

<210> SEQ ID NO 11
<211> LENGTH: 12
<212> TYPE: DNA
<213> ORGANISM: Nannochloropsis gaditana
```

-continued

```
<400> SEQUENCE: 11
tcaaacatgg ct                                                          12

<210> SEQ ID NO 12
<211> LENGTH: 12
<212> TYPE: DNA
<213> ORGANISM: Nannochloropsis gaditana

<400> SEQUENCE: 12
tcaaacatgg cg                                                          12

<210> SEQ ID NO 13
<211> LENGTH: 12
<212> TYPE: DNA
<213> ORGANISM: Artificial Sequence
<220> FEATURE:
<223> OTHER INFORMATION: Generic Nannochloropsis consensus Kozak
      sequence
<220> FEATURE:
<221> NAME/KEY: misc_feature
<222> LOCATION: (1)..(1)
<223> OTHER INFORMATION: Can be G or T.
<220> FEATURE:
<221> NAME/KEY: misc_feature
<222> LOCATION: (5)..(5)
<223> OTHER INFORMATION: Can be C or T.
<220> FEATURE:
<221> NAME/KEY: misc_feature
<222> LOCATION: (12)..(12)
<223> OTHER INFORMATION: Can be G or T.

<400> SEQUENCE: 13
kcaaycatgg ck                                                          12

<210> SEQ ID NO 14
<211> LENGTH: 12
<212> TYPE: DNA
<213> ORGANISM: Artificial Sequence
<220> FEATURE:
<223> OTHER INFORMATION: Generic Nannochloropsis consensus Kozak
      sequence
<220> FEATURE:
<221> NAME/KEY: misc_feature
<222> LOCATION: (1)..(1)
<223> OTHER INFORMATION: Can be G or T.
<220> FEATURE:
<221> NAME/KEY: misc_feature
<222> LOCATION: (5)..(5)
<223> OTHER INFORMATION: Can be A or C or T/U.
<220> FEATURE:
<221> NAME/KEY: misc_feature
<222> LOCATION: (12)..(12)
<223> OTHER INFORMATION: Can be G or T.

<400> SEQUENCE: 14
kcaahcatgg ck                                                          12

<210> SEQ ID NO 15
<211> LENGTH: 15
<212> TYPE: DNA
<213> ORGANISM: Artificial Sequence
<220> FEATURE:
<223> OTHER INFORMATION: Generic Nannochloropsis consensus Kozak
      sequence
<220> FEATURE:
<221> NAME/KEY: misc_feature
<222> LOCATION: (1)..(1)
<223> OTHER INFORMATION: Can be G or T.
<220> FEATURE:
<221> NAME/KEY: misc_feature
```

```
<222> LOCATION: (5)..(5)
<223> OTHER INFORMATION: Can be C or T.
<220> FEATURE:
<221> NAME/KEY: misc_feature
<222> LOCATION: (12)..(12)
<223> OTHER INFORMATION: Can be G or T.
<220> FEATURE:
<221> NAME/KEY: misc_feature
<222> LOCATION: (13)..(14)
<223> OTHER INFORMATION: n is a, c, g, or t

<400> SEQUENCE: 15
kcaaycatgg cknnc                                                         15

<210> SEQ ID NO 16
<211> LENGTH: 15
<212> TYPE: DNA
<213> ORGANISM: Artificial Sequence
<220> FEATURE:
<223> OTHER INFORMATION: Generic Nannochloropsis consensus Kozak
      sequence
<220> FEATURE:
<221> NAME/KEY: misc_feature
<222> LOCATION: (1)..(1)
<223> OTHER INFORMATION: Can be G or T.
<220> FEATURE:
<221> NAME/KEY: misc_feature
<222> LOCATION: (5)..(5)
<223> OTHER INFORMATION: Can be A or C or T/U.
<220> FEATURE:
<221> NAME/KEY: misc_feature
<222> LOCATION: (12)..(12)
<223> OTHER INFORMATION: Can be G or T.
<220> FEATURE:
<221> NAME/KEY: misc_feature
<222> LOCATION: (13)..(14)
<223> OTHER INFORMATION: n is a, c, g, or t

<400> SEQUENCE: 16
kcaahcatgg cknnc                                                         15

<210> SEQ ID NO 17
<211> LENGTH: 20
<212> TYPE: DNA
<213> ORGANISM: Artificial Sequence
<220> FEATURE:
<223> OTHER INFORMATION: Extended generic Nannochloropsis consensus
      Kozak sequence
<220> FEATURE:
<221> NAME/KEY: misc_feature
<222> LOCATION: (2)..(2)
<223> OTHER INFORMATION: Can be A or G.
<220> FEATURE:
<221> NAME/KEY: misc_feature
<222> LOCATION: (3)..(3)
<223> OTHER INFORMATION: Can be C or T.
<220> FEATURE:
<221> NAME/KEY: misc_feature
<222> LOCATION: (16)..(16)
<223> OTHER INFORMATION: Can be G or T.
<220> FEATURE:
<221> NAME/KEY: misc_feature
<222> LOCATION: (18)..(18)
<223> OTHER INFORMATION: Can be C or T.

<400> SEQUENCE: 17
crycgcaacc atggckgycg                                                    20

<210> SEQ ID NO 18
<211> LENGTH: 20
<212> TYPE: DNA
<213> ORGANISM: Nannochloropsis gaditana
```

```
<400> SEQUENCE: 18
caccgcaacc atggcggccg                                              20

<210> SEQ ID NO 19
<211> LENGTH: 20
<212> TYPE: DNA
<213> ORGANISM: Nannochloropsis gaditana

<400> SEQUENCE: 19
cctcgcaacc atggctgtcg                                              20

<210> SEQ ID NO 20
<211> LENGTH: 20
<212> TYPE: DNA
<213> ORGANISM: Nannochloropsis gaditana

<400> SEQUENCE: 20
cctcgcaacc atggctgccg                                              20
```

NANNOCHLOROPSIS KOZAK CONSENSUS SEQUENCE

REFERENCE TO A SEQUENCE LISTING

This application contains references to amino acid sequences and/or nucleic acid sequences which have been submitted concurrently herewith as the sequence listing text file "61486245_1.txt", file size 5 kilobytes (kb), created on 27 Apr. 2015. The aforementioned sequence listing is hereby incorporated by reference in its entirety pursuant to 37 C.F.R. §1.52(e)(ii).

FIELD

The present invention relates to regulatory elements for use in protein expression in eukaryotic cells, particularly algal cells.

BACKGROUND

Algal cells are a promising source of biofuels (Wijffels & Barbosa (2010) *Science* 329:796-99). Their ability to harness solar energy to convert carbon dioxide into carbon-rich lipids already exceeds the abilities of oil-producing agricultural crops, with the added advantage that algae grown for biofuel do not compete with oil-producing crops for agricultural land (Wijffels & Barbosa, 2010). In order to maximize algal fuel production, new algal strains will need to be engineered for growth and carbon fixation at an industrial scale (Wijffels & Barbosa, 2010). The identification of feasible regulatory elements is important to drive optimal protein expression relating to biofuel production in recombinant algae.

A Kozak sequence is a short consensus sequence centered around the translational initiation site of eukaryotic mRNAs that allows for efficient initiation of translation of the mRNA. The ribosomal translation machinery recognizes the AUG initiation codon in the context of the Kozak sequence, which differs among different phylogenetic groups. A sequence around the site of translational initiation that poorly matches the Kozak consensus for a species can reduce the level of translation and may result in the use of alternate or cryptic translational start sites that can interfere with translation of the transcript's major open reading frame.

Different mRNAs of the same organism can have slightly different Kozak sequences with different variations with respect to a consensus Kozak sequence for the organism, and the amount of protein synthesized from a given mRNA depends in part on the Kozak sequence's "strength." A Kozak sequence's strength depends, in turn, on the precise sequence of nucleic acids of which it is composed. Certain positions in the sequence are more important than others, for example, the "start codon" (adenine-uracil-guanine, abbreviated "AUG") is the most important portion of a Kozak sequence because AUG is the actual initiation codon encoding an N-terminal methionine. The A of the AUG is referred to as position +1 of a Kozak sequence, the U as position +2, etc. There is no number zero, so the position immediately upstream of the A is position −1. In vertebrates, a "strong" Kozak sequence in vertebrates requires a G in position +4 and an A or G in position −3. A Kozak sequence without either a G in position +4 or an A or G in position −3 will be "weak" when used in vertebrate gene expression. A vertebrate Kozak sequence with a G in position +4, or an A or G in position −3, but not both, is said to be "adequate." Other positions also have lesser effects on the comparative "strength" or "weakness" of translation from a given mRNA. See, Kozak (1986) *Cell* 44:283-92.

Kozak (1987) *Nucleic Acids Res.* 15:8125-48 first discovered the vertebrate Kozak consensus sequence by analyzing transcripts from vertebrate animals. Since then, investigators have identified a wide range of Kozak sequences, each unique to a particular class of organisms.

For example, Hamilton et al. (1987) *Nucleic Acids Res.* 15:3581-93 report a Kozak consensus sequence from yeast.

Lütcke et al. (1987) *EMBO J.* 6:43-48 1001 report a consensus Kozak sequences from terrestrial plants.

Joshi et al. (1997) *Plant Mol. Biol.* 35:993-1001 report a consensus Kozak sequences from terrestrial plants.

Bruchez et al. (1993) *Fungal Genet. Newslett.* 40:89-96 report consensus Kozak sequences from nuclear gene transcripts in *Neurospora crassa*.

Ikeda & Miyaska (1998) *Biosci. Biotechnol. Biochem.* 62:2457-59 report consensus Kozak sequences from both nuclear and chloroplastic transcripts collected from *Chlamydomonas reinhardtii*.

U.S. Pat. No. 7,449,568 to Fukuda et al. reports a possible Kozak sequence from *Porphyra yezoensis*.

Briggs & Tachikawa (U.S. Pub. No. 2010/0306880) report a single eukaryotic Kozak consensus sequence.

Tsai & Li (U.S. Pub. No. 2011/0014708) report the use of a mammalian Kozak sequence to drive translation of transgene transcripts in *Nannochloropsis oculata*.

However, to date, a Kozak consensus sequence in *Nannochloropsis* has not been identified.

SUMMARY

This section provides a general summary of the disclosure, and is not a comprehensive disclosure of its full scope or all of its features.

The present invention provides Kozak sequences for use in gene expression in eukaryotic cells, particularly heterokont and algal cells.

In one aspect, an isolated or recombinant DNA molecule is provided in which the isolated or recombinant DNA molecule comprises a nucleotide sequence according to of SEQ ID NO:13 or SEQ ID NO:14. The isolated or recombinant nucleic acid molecule can be a recombinant nucleic acid molecule that includes a Kozak sequence according to SEQ ID NO:13 or SEQ ID NO:14 operably linked to a heterologous nucleotide sequence encoding a polypeptide, in which the initiating methionine of the polypeptide is the codon ATG that is represented by positions 1, 2, and 3 of the Kozak sequence, where the numbering of the Kozak sequence is as provided in Tables 2, 3 and 5 herein. (The A of the ATG is referred to as position +1 of a Kozak sequence, the T as position +2, etc., and the position immediately upstream of the A is position −1.) In particular examples, the Kozak sequence can be selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12. Additionally, the recombinant nucleic acid molecule can comprise a translational initiation consensus sequence that includes a Kozak sequence such as any provided herein (e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12), where the translational initiation consensus sequence further includes a "C" at position 9, using Kozak sequence numbering. For example, the recombinant nucleic acid can comprise a translational initiation sequence according to SEQ ID NO:15 or SEQ ID NO:16. In further examples, the isolated or recombinant nucleic acid molecule can be a recombinant nucleic acid molecule that includes a Kozak sequence according to SEQ ID NO:17 operably linked to a heterologous nucleotide sequence encoding a polypeptide, in which the initiating methionine of the polypeptide is the codon ATG that is represented by positions 1, 2, and 3 of the Kozak sequence. In illustrative examples, the isolated or recombinant nucleic acid molecule can be a recombinant nucleic acid molecule that includes a Kozak sequence according to SEQ ID NO:18, SEQ ID NO:19, or SEQ ID NO:20.

A Kozak sequence as provided herein can enhance translation in a eukaryotic cell of a transcript into which it is incorporated. For example, a Kozak sequence as provided herein can be integrated into a DNA molecule that encodes a polypeptide, wherein the Kozak sequence is heterologous with respect to the polypeptide-encoding sequence, such that the heterologous Kozak sequence is operably linked to the polypeptide-encoding sequence, such that when the DNA molecule is transcribed, the heterologous Kozak sequence is part of the mRNA transcript, such that positions 1, 2, and 3 of the Kozak sequence make up the initiating methionine codon of the transcript. The use of a Kozak sequence as provided herein in a DNA molecule encoding a polypeptide may enhance translation of the corresponding mRNA transcript that includes the polypeptide-encoding sequence in a eukaryotic cell. For example, a heterologous Kozak sequence as provided herein may enhance translation of an mRNA transcript in a plant cell. Additionally or alternatively, a heterologous Kozak sequence as provided herein may enhance translation of an mRNA transcript into which it is incorporated in a heterokont cell. Further additionally or alternatively, a heterologous Kozak sequence as provided herein may enhance translation of an mRNA transcript in an algal cell. Enhanced translation of an mRNA transcript can be reflected, for example, in increased abundance of the protein encoded by the mRNA transcript.

Also provided herein is an expression construct comprising a promoter and a heterologous Kozak sequence according to any of SEQ ID NO:13, SEQ ID NO:14, SEQ ID NO:15, SEQ ID NO:16, or SEQ ID NO:17, in which the heterologous Kozak sequence is located in a position downstream of the promoter. For example, an expression construct can include a heterologous Kozak sequence of SEQ ID NO:1, 2, 3, 4, 5, 6, 7, 8, 9, 10, 11, 12, 18, 19, or 20, in which the heterologous Kozak sequence of SEQ ID NO:1, 2, 3, 4, 5, 6, 7, 8, 9, 10, 11, 12, 18, 19, or 20 is positioned in a position downstream of the promoter. For example, the expression construct provided herein may comprise a promoter upstream of a heterologous Kozak sequence of SEQ ID NO:1, a promoter upstream of a heterologous Kozak sequence of SEQ ID NO:2, a promoter upstream of a heterologous Kozak sequence of SEQ ID NO:3, a promoter upstream of a heterologous Kozak sequence of SEQ ID NO:4, a promoter upstream of a heterologous Kozak sequence of SEQ ID NO:5, a promoter upstream of a heterologous Kozak sequence of SEQ ID NO:6, a promoter upstream of a heterologous Kozak sequence of SEQ ID NO:7, a promoter upstream of a heterologous Kozak sequence of SEQ ID NO:8, a promoter upstream of a heterologous Kozak sequence of SEQ ID NO:9, a promoter upstream of a heterologous Kozak sequence of SEQ ID NO:10, a promoter upstream of a heterologous Kozak sequence of SEQ ID NO:11, a promoter upstream of a heterologous Kozak sequence of SEQ ID NO:12, a promoter upstream of a heterologous Kozak sequence of SEQ ID NO:18, a promoter upstream of a heterologous Kozak sequence of SEQ ID NO:19, or a promoter upstream of a heterologous Kozak sequence of SEQ ID NO:20. The expression construct as provided herein may be optionally made part of a vector for cloning, transfection and/or expression in a eukaryotic cell, and which can optionally include one or more of an origin of replication, a sequence mediating recombination into a host genome, or a selectable marker.

Also provided herein is an expression cassette. The expression cassette comprises a eukaryotic promoter, a heterologous Kozak sequence as disclosed herein, and a nucleotide sequence encoding a polypeptide operably linked to the promoter and the heterologous Kozak sequence. The eukaryotic promoter can be a promoter that is active in a heterokont or a eukaryotic microalga. Additionally or alternatively, the promoter can be a Simian vacuolating virus (SV40) promoter, a cauliflower mosaic virus (CaMV) promoter, a cytomegalovirus (CMV) promoter, a promoter derived from a heterokont species, or a promoter derived from a green algal species. Further additionally or alternatively, the promoter can be derived from a heterokont species of the genus *Nannochloropsis*. The expression cassette can further optionally comprise a nucleic acid sequence comprising a terminator sequence. In various examples, the expression cassette can include a nucleotide sequence encoding (a) protein associated with lipid biosynthesis, (b) a polyptepide having lipolytic activity, (c) a protein that participates in photosynthesis, (d) a protein associated with carbon fixation, (e) a transporter protein, (f) a dehydrogenase, (g) a transcription factor, or (h) a protein involved in cell signaling. The gene can be codon-optimized for expression in a heterokont or an alga. The expression cassette can be provided in a vector, e.g., an expression vector, which can optionally include one or more of an origin of replication, sequences mediating recombination into a host genome, or a selectable marker.

Further provided herein is a vector, e.g. an expression or transformation vector, for eukaryotic cell transformation that comprises an expression cassette in which a Kozak sequence as disclosed herein is operably linked to a gene of interest, wherein the Kozak sequence is heterologous with respect to the gene of interest. The vector can further include a terminator operably linked to the coding sequence of the gene of interest. The vector can optionally include a gene encoding a selectable marker or a reporter gene. The gene encoding a selectable marker can encode a polypeptide that confers resistance to an antibiotic, a polypeptide that confers tolerance to an herbicide, a gene encoding an auxotrophic marker, or any other gene product that can allow for selection of transformants. A gene encoding a reporter can, for example, encode a fluorescent protein or an enzyme that can produce a detectable product.

Also provided herein is a method for transforming a eukaryotic cell. The method comprises: (1) introducing a transformation vector that includes a selectable marker and a heterologous Kozak sequence as provided herein operably linked to a gene of interest; and (2) selecting for a transformant. For example, the eukaryotic cell can be transformed by means of electroporation or a biolistic procedure. The eukaryotic cell can be selected from the group consisting of a fungi cell, a heterokont cell, an algal cell, and a plant cell. In a particular embodiment the eukaryotic cell is an algal cell.

For example, an algal cell that can be transformed with a transformation vector as provided herein can be selected from the group consisting of species of the genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella,*

*Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox*. For example, the algal cell can be a diatom, such as for example, an *Amphora, Chaetoceros, Cyclotella, Fragilaria, Navicula, Nitzschia, Phaeodactylum*, or *Thalassiosira*. Alternatively, the algal cell can be a green algal cell, for example, a *Tetraselmis* cell, a *Dunaliella* cell, or a *Chlorella* cell. In further examples, the algal cell can be an *Ellipsoidon* cell or a *Nannochloropsis* cell.

Also provided is a eukaryotic microorganism transformed with an expression vector or transformation vector as provided herein. The eukaryotic microorganism can be a fungus, an alga, or a plant. Additionally or alternatively, the eukaryotic microorganism can be a heterokont or microalga, such as but not limited to for example, a *Nannochloropsis* cell.

For example, the eukaryotic microorganism transformed with a vector as provided herein can be selected from the group consisting of species of genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox*. For example, the algal cell can be a green algal cell, for example, a *Tetraselmis* cell, a *Dunaliella* cell, or a *Chlorella* cell. In further examples, the algal cell can be an *Ellipsoidon* cell or a *Nannochloropsis* cell.

Also provided is a method of expressing a protein of interest in a eukaryotic cell. The method provided herein comprises transfecting a eukaryotic cell with an expression vector comprising an expression cassette as provided herein, and providing conditions under which the nucleotide sequence encoding the polypeptide is expressed. The eukaryotic cell can be a fungus, an alga, or a plant cell. Additionally or alternatively, the eukaryotic cell can be a heterokont or microalga, such as but not limited to for example, a *Nannochloropsis* cell. The protein of interest expressed by the cell can be, for example: (a) a protein associated with lipid biosynthesis; (b) a polypeptide having lipolytic activity; (c) a protein that participates in photosynthesis; (d) a protein associated with carbon fixation; (e) a transporter protein; (f) a dehydrogenase; (g) a transcription factor; or (h) a cell signaling protein.

For example, the eukaryotic microorganism used to express a protein of interest can be selected from the group consisting of species of genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox*. For example, the algal cell can be an *Ellipsoidon* cell, a *Nannochloropsis* cell, or a *Tetraselmis* cell.

The method of expressing a protein of interest as provided herein can enhance protein expression relative to expression from cells without the vectors of the present invention. For example, the method of expressing a protein of interest as provided herein can enhance protein expression at least 5% relative to expression achieved from a substantially identical eukaryotic cell transformed with a vector substantially identical to a vector of the present invention, except for the absence of a heterologous Kozak sequence selected from the group of SEQ ID NOs:1, 2, 3, 4, 5, 6, 7, 8, 9, 10, 11, 12, 18, 19, or 20. Additionally or alternatively, the method of expressing a protein of interest as provided herein can enhance protein expression at least 10%, at least 20%, at least 30%, at least 40%, at least 50%, or at least 60% relative to expression achieved from a substantially identical eukaryotic cell transformed with a vector substantially identical to a vector of the present invention, except for the absence of a heterologous Kozak sequence selected from the group of SEQ ID NOs:1, 2, 3, 4, 5, 6, 7, 8, 9, 10, 11, 12, 18, 19, or 20.

Further areas of applicability will become apparent from the description provided herein. The description and specific examples in this summary are intended for purposes of illustration only and are not intended to limit the scope of the present disclosure.

DETAILED DESCRIPTION

A. Definitions

Figure 1:
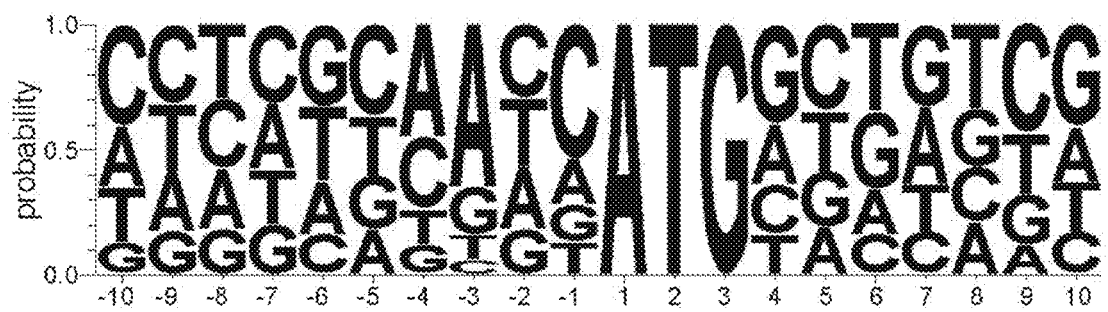
FIG. 1 is a graphical representation of the occupancy percentage of each nucleotide at each position from −10 to +10 around the canonical ATG start codon in the 100 most abundant *Nannochloropsis* transcripts. The relative size of each letter corresponds to the frequency with which the indicated nucleotide is found in the indicated position in the *Nannochloropsis* 100 most highly expressed genes of the transcriptome.

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

To facilitate an understanding of the present invention, a number of terms and phrases are defined below.

As used in the present disclosure and claims, the singular forms "a," "an," and "the" include plural forms unless the context clearly dictates otherwise.

Wherever embodiments are described herein with the language "comprising," otherwise analogous embodiments described in terms of "consisting of" and/or "consisting essentially of" are also provided.

The term "and/or" as used in a phrase such as "A and/or B" herein is intended to include "A and B", "A or B", "A", and "B".

The terms "cells", "cell cultures", "cell line", "recombinant host cells", "recipient cells" and "host cells" as used herein include the primary subject cells and any progeny thereof, without regard to the number of transfers. It should be understood that not all progeny are exactly identical to the parental cell (due to deliberate or inadvertent mutations or differences in environment); however, such altered progeny are included in these terms, so long as the progeny retain the same functionality as that of the originally transformed cell.

The term "gene" is used broadly to refer to any segment of nucleic acid (typically DNA, but optionally RNA) encoding a protein or expressed RNA. Thus, genes include sequences encoding expressed RNA (which can include polypeptide coding sequences as well as functional RNA sequences). Genes may further comprise the regulatory sequences required for their expression. Genes can be obtained from a variety of sources, including cloning from a source of interest or synthesizing from known or predicted sequence information, and may include sequences designed to have desired parameters. The terms "protein" and "polypeptide" are used interchangeably herein.

The terms "nucleic acid" or "nucleic acid molecule" refer to, e.g., DNA or RNA (e.g., mRNA). The nucleic acid molecules can be double-stranded or single-stranded; single stranded RNA or DNA can be the coding (sense) strand or the non-coding (antisense) strand.

The terms "coding sequence" or "coding region" as used herein, refer to a region of a DNA sequence that can be transcribed to produce an mRNA transcript that can be translated into an amino acid sequence, e.g., of a peptide or polypeptide or an RNA transcript that can be translated into an amino acid sequence, e.g., of a peptide or a polypeptide. The term "non-coding sequence" or "non-coding region" refers to (1) a region of a DNA sequence that, if transcribed, is not translated into an amino acid sequence (e.g., introns, untranslated regions, etc.); or (2) a region of an RNA sequence that is not translated into amino acids. For simplicity and brevity, a sequence that "encodes a polypeptide" refers to a DNA sequence that can be transcribed and translated to produce the polypeptide or an RNA sequence that can be translated to produce the polypeptide, whereas a sequence that "encodes a functional RNA" refers to a DNA sequence that when transcribed produces a functional RNA molecule. An RNA molecule that encodes a polypeptide or functional RNA can be further processed prior to, or concomitant with, translation into a polypeptide or formation of the mature functional RNA.

A "functional RNA molecule" is an RNA molecule that can interact with one or more proteins or nucleic acid molecules to perform or participate in a structural, catalytic, or regulatory function that affects the expression or activity of a gene or gene product other than the gene that produced the functional RNA. A functional RNA can be, for example, a transfer RNA (tRNA), ribosomal RNA (rRNA), anti-sense RNA (as-RNA), microRNA (miRNA), short-hairpin RNA (shRNA), small interfering RNA (siRNA), small nucleolar RNAs (snoRNAs), piwi-interacting RNA (piRNA), or a ribozyme.

A biomolecule may be "derived from" an indicated source, which includes the isolation (in whole or in part) of a nucleic acid segment from an indicated source or the purification of a polypeptide from an indicated source. A nucleic acid molecule may also be derived from an indicated source by, for example, direct cloning, PCR amplification, or artificial synthesis from the indicated polynucleotide source or based on a sequence associated with the indicated polynucleotide source. Genes or nucleic acid molecules derived from a particular source or species also include genes or nucleic acid molecules having sequence modifications with respect to the source nucleic acid molecules. For example, a gene or nucleic acid molecule derived from a source (e.g., a particular referenced gene) can incur one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other molecular biology techniques, or by chemical synthesis. A gene or nucleic acid molecule that is derived from a referenced gene or nucleic acid molecule that encodes a functional RNA or polypeptide can encode a functional RNA or polypeptide having at least 70%, at least 75%, at least 80%, at least 85%, at least 90%, at least 95%, at least 96%, at least 97%, at least 98%, or at least 99% sequence identity with the referenced or source functional RNA or polypeptide, or to a functional fragment thereof. For example, a gene or nucleic acid molecule that is derived from a referenced gene or nucleic acid molecule that encodes a functional RNA or polypeptide can encode a functional RNA or polypeptide having at least 85%, at least 90%, at least 95%, at least 96%, at least 97%, at least 98%, or at least 99% sequence identity with the referenced or source functional RNA or polypeptide, or to a functional fragment thereof.

The term "isolated", such as an isolated protein or nucleic acid as used herein, refers to a biomolecule removed from the context in which the biomolecule exists in nature. An isolated biomolecule can be, in some instances, partially or substantially purified. For example, an isolated nucleic acid molecule can be a nucleic acid sequence that has been excised from the chromosome, genome, or episome into which it is integrated in nature.

A "purified" nucleic acid molecule or nucleotide sequence, or protein or polypeptide sequence, is substantially free of cellular material and cellular components. The purified nucleic acid molecule or protein may be free of chemicals beyond buffer or solvent, for example. "Substantially free" is not intended to mean that other components beyond the novel nucleic acid molecules are undetectable.

The terms "naturally-occurring" and "wild-type" (WT) refer to a form found in nature. For example, a naturally occurring or wild-type nucleic acid molecule, nucleotide sequence, or protein may be present in, and isolated from, a natural source, and is not intentionally modified by human manipulation.

"Exogenous nucleic acid molecule" or "exogenous gene" refers to a nucleic acid molecule or gene that has been introduced ("transformed") into a cell. A transformed cell may be referred to as a "recombinant" cell, into which additional exogenous gene(s) may be introduced. A descendent of a cell transformed with a nucleic acid molecule is also referred to as "transformed" if it has inherited the exogenous nucleic acid molecule. The exogenous gene may be from a different species (and may in this context be described as "heterologous" with respect to the host organism), or from the same species (and so may in this context be described as "homologous" with respect to the host organism), relative to the cell being transformed. An "endogenous" nucleic acid molecule, gene, or protein is a native nucleic acid molecule, gene, or protein as it occurs in, or is naturally produced by, the host.

Further, the term "exogenous" as used herein in the context of a gene or protein, refers to a gene or protein that is not derived from the host organism species.

The term "transgene" as used herein refers to an exogenous gene, that is, a gene introduced into a microorganism or a progenitor by human intervention.

The term "ortholog" of a gene or protein as used herein refers to its functional equivalent in another species.

The term "native" is used herein to refer to nucleic acid sequences or amino acid sequences as they naturally occur in the host. The term "non-native" is used herein to refer to nucleic acid sequences or amino acid sequences that do not occur naturally in the host. A nucleic acid sequence or amino acid sequence that has been removed from a host cell, subjected to laboratory manipulation, and reintroduced into a host cell is considered "non-native." Non-native genes include genes endogenous to the host microorganism operably linked to one or more heterologous regulatory sequences that have been inserted into the host genome.

The term "heterologous" when used in reference to a polynucleotide, a gene, a nucleic acid, a polypeptide, or an enzyme refers to a polynucleotide, gene, a nucleic acid, polypeptide, or an enzyme not derived from the host species. When referring to a gene regulatory sequence or to an auxiliary nucleic acid sequence used for maintaining or manipulating a gene sequence (e.g. a 5' untranslated region, 3' untranslated region, Kozak sequence, poly A addition sequence, intron sequence, splice site, ribosome binding site, internal ribosome entry sequence, genome homology region, recombination site, etc.), "heterologous" means that the regulatory sequence or auxiliary sequence is from a different source than the gene with which the regulatory or auxiliary nucleic acid sequence is juxtaposed in a construct, genome, chromosome or episome. Thus, a Kozak sequence operably linked to a gene to which it is not operably linked in its natural state (i.e. in the genome of a non-genetically engineered organism) is referred to herein as a "heterologous Kozak sequence," even though the promoter may be derived from the same species (or, in some cases, the same organism) as the gene to which it is linked. Similarly, when referring to a protein localization sequence of an engineered protein, "heterologous" means that the localization sequence is derived from a protein different from that into which it is incorporated by genetic engineering.

The term "recombinant" or "engineered" nucleic acid molecule as used herein, refers to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, digestion (exonucleolytic or endonucleolytic), ligation, reverse transcription, transcription, base modification (including, e.g., methylation), or recombination (including homologous and site-specific recombination)) of nucleic acid molecules; 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering.

When applied to organisms, the terms "transgenic" or "recombinant" or "engineered" or "genetically engineered" refer to organisms that have been manipulated by introduction into the organism of an exogenous or recombinant nucleic acid sequence. For example, a transgenic microorganism can include an introduced exogenous regulatory sequence operably linked to an endogenous gene of the transgenic microorganism. Non-limiting examples of such manipulations include gene knockouts, targeted mutations and gene replacement, promoter replacement, deletion, or insertion, as well as introduction of transgenes into the organism. Recombinant or genetically engineered organisms can also be organisms into which constructs for gene "knock down" have been introduced. Such constructs include, but are not limited to, RNAi, microRNA, shRNA, antisense, and ribozyme constructs. Also included are organisms whose genomes have been altered by the activity of meganucleases or zinc finger nucleases. A heterologous or recombinant nucleic acid molecule can be integrated into a recombinant/genetically engineered organism's genome or, in other instances, not integrated into a recombinant/genetically engineered organism's genome. As used herein, "recombinant microorganism" or "recombinant host cell" includes progeny or derivatives of the recombinant microorganisms of the invention. Because certain modifications may occur in succeeding generations from either mutation or environmental influences, such progeny or derivatives may not, in fact, be identical to the parent cell, but are still included within the scope of the term as used herein.

"Regulatory sequence", "regulatory element", or "regulatory element sequence" refers to a nucleotide sequence located upstream (5'), within, or downstream (3') of a coding sequence. Transcription of the coding sequence and/or translation of an RNA molecule resulting from transcription of the coding sequence are typically affected by the presence or absence of the regulatory sequence. These regulatory element sequences may comprise promoters, cis-elements, enhancers, Kozak sequences, terminators, or introns. Regulatory elements may be isolated or identified from UnTranslated Regions (UTRs) from a particular polynucleotide sequence. Any of the regulatory elements described herein may be present in a chimeric or hybrid regulatory expression element. Any of the regulatory elements described herein may be present in a recombinant construct of the present invention.

The term "Kozak sequence" refers to an element located within an mRNA transcript that helps ribosomal translation machinery to recognize where on the transcript translation should begin (see, Kozak, 1987). Translation begins with the "start codon" of the Kozak sequence: adenosine-uracil-guanine, so the positions of the Kozak sequence are numbered according to the positions relative to the adenosine (+1) at the 5' end of the start codon. The position immediately downstream of the adenosine is position +2, the next most downstream is position +3, etc. The position immediately upstream of the adenosine is position -1, the next most upstream is position -2, etc. There is no position zero.

The terms "promoter", "promoter region", or "promoter sequence" are used interchangeably herein and refer to a nucleic acid sequence capable of binding RNA polymerase to initiate transcription of a gene in a 5' to 3' ("downstream") direction. A gene is "under the control of" or "regulated by" a promoter when the binding of RNA polymerase to the promoter is the proximate cause of said gene's transcription. The promoter or promoter region typically provides a recognition site for RNA polymerase and other factors necessary for proper initiation of transcription. A promoter may be isolated from the 5' untranslated region (5' UTR) of a genomic copy of a gene. Alternatively, a promoter may be synthetically produced or designed by altering known DNA elements. Also considered are chimeric promoters that combine sequences of one promoter with sequences of another promoter. Promoters may be defined by their expression pattern based on, for example, metabolic, environmental, or developmental conditions. A promoter can be used as a regulatory element for modulating expression of an operably linked transcribable polynucleotide molecule, e.g., a coding sequence. Promoters may contain, in addition to sequences recognized by RNA polymerase and (preferably) other transcription factors, regulatory sequence elements such as cis-elements or enhancer domains that affect the transcription of operably linked genes. An "algal promoter" is a native or non-native promoter that is functional in algal cells.

The term "constitutive" as used herein, refers to a promoter that is active under most environmental and developmental conditions. A constitutive promoter is active regardless of external environment, such as light and medium. In some examples, a constitutive promoter is active in the presence and in the absence of a nutrient. For example, a constitutive promoter may be a promoter that is active (mediates transcription of a gene to which it is operably-linked) under conditions of nitrogen depletion as well as under conditions in which nitrogen is not limiting (nitrogen replete conditions). In contrast, an "inducible" promoter is a promoter that is active in response to particular environmental conditions, such as the presence or absence of a nutrient or regulator, the presence of light, etc.

The term "operably linked" as used herein denotes a configuration in which a regulatory sequence is placed at an appropriate position relative to a polynucleotide sequence such that the regulatory sequence affects or directs expression of the polynucleotide sequence, for example, to produce a polypeptide and/or functional RNA. Thus, a promoter is in operable linkage with a nucleic acid sequence if it can mediate transcription of the nucleic acid sequence. A Kozak sequence is in operable linkage with a coding sequence when the ATG sequence of the Kozak sequence is the initiating methionine codon of the gene. When introduced into a host cell, an expression cassette can result in transcription and/or translation of an encoded RNA or polypeptide under appropriate conditions. Antisense or sense constructs that are not or cannot be translated are not excluded by this definition.

The term "expression construct" as used herein refers to a nucleic acid construct comprising a Kozak sequence downstream of a promoter. An expression construction may be placed in a cloning vector (into which a DNA fragment can be inserted) or an expression/transformation vector (used to control expression of a particular gene).

The term "expression cassette" as used herein refers to a nucleic acid construct that contains a nucleic acid sequence encoding a protein or functional RNA (e.g., a tRNA, a short hairpin RNA, one or more microRNAs, a ribosomal RNA, etc.) operably linked to expression control elements, such as a promoter, and optionally, any or a combination of other nucleic acid sequences that affect transcription or translation, such as, but not limited to, a transcriptional terminator, a ribosome binding site, a splice site or splicing recognition sequence, an intron, an enhancer, a polyadenylation signal, an internal ribosome entry site, etc. An expression cassette may comprise an expression construct.

The term "vector" as used herein refers to a nucleic acid construct that is structured so as to facilitate movement of nucleic acids from one environment, intracellular or extracellular, to another environment, intracellular or extracellular. A vector optimized for use in modifying portions of the nucleic acid is a "cloning vector." A vector optimized for use in transforming a cell or expressing a gene of interest in a cell is a "transformation vector" or an "expression vector," these two terms being used interchangeably herein. A vector may optionally include one or more of: an origin of replication; a sequence mediating recombination into a host genome; or a selectable marker As used herein "attenuated" means reduced in amount, degree, intensity, or strength. Attenuated gene expression may refer to a significantly reduced amount and/or rate of transcription of the gene in question, or of translation, folding, or assembly of the encoded protein. As nonlimiting examples, an attenuated gene may be a mutated or disrupted gene (e.g., a gene disrupted by partial or total deletion, insertional mutation, or meganuclease disruption), or a gene having decreased expression resulting from alteration of gene regulatory sequences. An attenuated gene may also be a gene that is targeted by a "gene knockdown" construct, such as, for example, a construct encoding an antisense RNA, a microRNA, a short hairpin RNA, or a ribozyme. In the case of both expression of transgenes and suppression of endogenous genes (e.g., by antisense or sense suppression) one of ordinary skill will recognize that the inserted polynucleotide sequence need not be identical, but may be only substantially identical to a sequence of the gene from which it was derived.

As explained herein, these substantially identical variants are specifically covered by reference to a specific nucleic acid sequence.

The term "microorganism" as used herein refers to any organism that is microscopic, i.e. too small to be seen by the naked eye. As used herein, the term "microorganism" may also refer to macroscopic organisms taxonomically related to microscopic organisms within the categories of yeast, heterokonts, algae, plants, bacteria, and fungi (including lichens). A microorganism may be unicellular or multicellular. A microorganism may be a bacterium, rickettsia, protozoon, or fungus. The term "microorganism" also includes microscopic plants and animals such as plankton, planaria, and amoebae, as well as arthropods such as dust mites, spider mites, etc.

The term "photosynthetic organism" as used herein is any prokaryotic or eukaryotic organism that can perform photosynthesis.

The terms "eukaryotic" and "eukaryote" are used in their broadest sense to include any organisms containing membrane bound nuclei and membrane bound organelles. Examples of eukaryotes include but are not limited to plants, yeast, animals, algae, diatoms, and fungi.

The terms "prokaryote" and "prokaryotic" are used in their broadest sense to include any organisms without a distinct nucleus. Examples of prokaryotes include but are not limited to bacteria, blue-green algae, archaebacteria, actinomycetes, and mycoplasma. Photosynthetic organisms include higher plants (i.e., vascular plants), bryophytes, algae, and photosynthetic bacteria.

The term "algae" includes, but is not limited to, a species of Bacillariophyceae (diatoms), Bolidomonas, Chlorophyceae (green algae), Chrysophyceae (golden algae), Cyanophyceae (cyanobacteria), Eustigmatophyceae (pico-plankton), Glaucocystophytes, Pelagophytes, Phaeophyceae (brown algae), Prasinophyceae (pico-plankton), Raphidophytes, Rhodophyceae (red algae), Synurophyceae, and Xanthophyceae (yellow-green algae). The term "algae" includes microalgae. The term "microalgae" as used herein refers to microscopic, single-celled algae species including, but not limited to, Bacillariophyceae, Chlorophyceae, Prasinophyceae and Eustigmatophyceae. The term "photosynthetic bacteria" includes, but is not limited to, cyanobacteria, green sulfur bacteria, purple sulfur bacteria, purple non-sulfur bacteria, and green non-sulfur bacteria.

The term "selectable marker" or "selectable marker gene" as used herein includes any gene that confers a phenotype on a cell in which it is expressed to facilitate the selection of cells that are transfected or transformed with a nucleic acid construct of the invention. The term may also be used to refer to gene products that effectuate said phenotypes. Examples of selectable markers include:

genes conferring resistance to antibiotics such as amikacin (aphA6), ampicillin (amp$^R$), blasticidin (bls, bsr, bsd), bleomicin or phleomycin (ZEOCIN™) (ble), chloramphenicol (cat), emetine (RBS 14p or cry1-1), erythromycin (ermE), G418 (GENETICIN™) (neo), gentamycin (aac3 or aacC4), hygromycin B (aphIV, hph, hpt), kanamycin (nptII), methotrexate (DHFR mtx$^R$), penicillin and other β-lactams (β-lactamases), streptomycin or spectinomycin (aadA, spec/strep), and tetracycline (tetA, tetM, tetQ);

genes conferring tolerance to herbicides such as aminotriazole, amitrole, andrimid, aryloxyphenoxy propionates, atrazines, bipyridyliums, bromoxynil, cyclohexandione oximes dalapon, dicamba, diclfop, dichlorophenyl dimethyl urea (DCMU), difunone, diketonitriles, diuron, fluridone, glufosinate, glyphosate, halogenated hydrobenzonitriles, haloxyfop, 4-hydroxypyridines, imidazolinones, isoxasflutole, isoxazoles, isoxazolidinones, miroamide B, p-nitrodiphenylethers, norflurazon, oxadiazoles, m-phenoxybenzamides, N-phenyl imides, pinoxadin, protoporphyrionogen oxidase inhibitors, pyridazinones, pyrazolinates, sulfonylureas, 1,2,4-triazol pyrimidine, triketones, urea; acetyl CoA carboxylase (ACCase), acetohydroxy acid synthase (ahas), acetolactate synthase (als, csr1-1, csr1-2, imr1, imr2), aminoglycoside phosphotransferase (apt), anthranilate synthase, bromoxynil nitrilase (bxn), cytochrome P450-NADH-cytochrome P450 oxidoreductase, dalapon dehalogenase (dehal), dihydropteroate synthase (sul), class I 5-enolpyruvylshikimate-3-phosphate synthase (EPSPS), class II EPSPS (aroA), non-class I/II EPSPS, glutathione reductase, glyphosate acetyltransferase (gat), glyphosate oxidoreductase (gox), hydroxyphenylpyruvate dehydrogenase, hydroxy-phenylpyruvate dioxygenase (hppd), isoprenyl pyrophosphate isomerase, lycopene cyclase, phosphinothricin acetyl transferase (pat, bar), phytoene desaturase (cal), prenyl transferase, protoporphyrin oxidase, the psbA photosystem II polypeptide (psbA), and SMM esterase (SulE) superoxide dismutase (sod);

genes that may be used in auxotrophic strains or to confer other metabolic effects, such as arg7, his3, hisD, hisG, lysA, manA, metE, nit1, trpB, ura3, xylA, a dihydrofolate reductase gene, a mannose-6-phosphate isomerase gene, a nitrate reductase gene, or an ornithine decarboxylase gene; a negative selection factor such as thymidine kinase; or toxin resistance factors such as a 2-deoxyglucose resistance gene.

A "reporter gene" is a gene encoding a protein that is detectable or has an activity that produces a detectable product. A reporter gene can encode a visual marker or enzyme that produces a detectable signal, such as cat, lacZ, uidA, xylE, an alkaline phosphatase gene, an α-amylase gene, an α-galactosidase gene, a β-glucuronidase gene, a β-lactamase gene, a horseradish peroxidase gene, a luciferin/luciferase gene, an R-locus gene, a tyrosinase gene, or a gene encoding a fluorescent protein, including but not limited to a blue, cyan, green, red, or yellow fluorescent protein, a photoconvertible, photoswitchable, or optical highlighter fluorescent protein, or any of variant thereof, including codon-optimized, rapidly folding, monomeric, increased stability, and enhanced fluorescence variants.

The term "terminator" or "terminator sequence" or "transcription terminator" as used herein refers to a regulatory section of genetic sequence that causes RNA polymerase to cease transcription.

The term "transformation" as used herein refers to the introduction of one or more exogenous nucleic acid sequences or polynucleotides into a host cell or organism by using one or more physical, chemical, or biological methods. Physical and chemical methods of transformation (i.e., "transfection") include, by way of non-limiting example, electroporation and liposome delivery. Biological methods of transformation (i.e., "transduction") include transfer of DNA using engineered viruses or microbes (e.g., *Agrobacterium*).

The terms, "identical" or percent "identity", in the context of two or more nucleic acids or polypeptide sequences, refer to two or more sequences or subsequences that are the same or have a specified percentage of amino acid residues or nucleotides that are the same, when compared and aligned for maximum correspondence over a comparison window. The degree of amino acid or nucleic acid sequence identity can be determined by various computer programs for aligning the sequences to be compared based on designated program parameters. For example, sequences can be aligned and compared using the local homology algorithm of Smith & Waterman (1981) *Adv. Appl. Math.* 2:482-89, the homology alignment algorithm of Needleman & Wunsch (1970) *J. Mol. Biol.* 48:443-53, or the search for similarity method of Pearson &

Lipman (1988) *Proc. Nat'l. Acad. Sci. USA* 85:2444-48, and can be aligned and compared based on visual inspection or can use computer programs for the analysis (for example, GAP, BESTFIT, FASTA, and TFASTA in the Wisconsin Genetics Software Package, Genetics Computer Group, 575 Science Dr., Madison, Wis.).

The BLAST algorithm, described in Altschul et al. (1990) *J. Mol. Biol.* 215:403-10, is publicly available through software provided by the National Center for Biotechnology Information (available at, www.ncbi.nlm.nih.gov). This algorithm identifies high scoring sequence pairs (HSPS) by identifying short words of length W in the query sequence, which either match or satisfy some positive-valued threshold score T when aligned with a word of the same length in a database sequence. T is referred to as the neighborhood word score threshold (Altschul et al., 1990). Initial neighborhood word hits act as seeds for initiating searches to find longer HSPs containing them. The word hits are then extended in both directions along each sequence for as far as the cumulative alignment score can be increased. Cumulative scores are calculated for nucleotides sequences using the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For determining the percent identity of an amino acid sequence or nucleic acid sequence, the default parameters of the BLAST programs can be used. For analysis of amino acid sequences, the BLASTP defaults are: word length (W), 3; expectation (E), 10; and the BLOSUM62 scoring matrix. For analysis of nucleic acid sequences, the BLASTN program defaults are word length (W), 11; expectation (E), 10; M=5; N=-4; and a comparison of both strands. The TBLASTN program (using a protein sequence to query nucleotide sequence databases) uses as defaults a word length (W) of 3, an expectation (E) of 10, and a BLOSUM 62scoring matrix. (see Henikoff & Henikoff (1989) *Proc. Nat'l. Acad. Sci. USA* 89:10915-19).

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873-87). The smallest sum probability (P(N)), provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, preferably less than about 0.01, and more preferably less than about 0.001.

Transcript abundance can be measured in terms of reads per kilobase of exon model per million mapped reads ("RPKM") (Mortazavi et al. (2008) *Nat. Methods* 5:621-28). RPKM for a gene is calculated by dividing the gene's total number of exon reads by the product of the number of mapped reads of that gene (in millions) multiplied by the exon length (in kilobases). A gene's total number of exon reads is the number of reads that have been mapped to a region in which an exon is annotated for the gene or across the boundaries of two exons or an intron and an exon for an annotated transcript of the gene. The mapped reads include all the reads uniquely mapped to the region of the gene as well as those of the reads which match in more places that have been allocated to the gene's region. Exon length is calculated as the sum of the lengths of all exons annotated for the gene. Each exon is included only once in this sum, even if it is present in more annotated transcripts for the gene. Partly overlapping exons count for their full length, even though they share the same region.

B. Nucleotide Sequences

Optimal expression of gene products can be achieved through the use of translation regulatory elements such as Kozak sequences. Novel heterologous Kozak sequences for use in enhancing recombinant protein expression in eukaryotic species, such as heterokont and microalgal species, including *Nannochloropsis*, are provided herein. Such sequences can aid in the efficient and consistent production of recombinant proteins by these hosts. Transformed heterokont or algal cells can be used, for example, for synthesis of various products including lipids.

Kozak sequences were identified from *Nannochloropsis* mRNAs. The method by which these new Kozak sequences were discovered is described more fully in Examples 1 and 2 herein. SEQ ID NOs:1-12 were discovered as comprising consensus Kozak sequences in the *Nannochloropsis* transcriptome. SEQ ID NOs:18-20 are extended translation initiation consensus sequences derived from analysis of the *Nannochloropsis* transcriptome and proteome. Table 1 summarizes these findings; the start codon of each Kozak sequence is underlined and highly conserved residues are shown in boldface. Consensus sequences encompassing the individual sequence provided in Table 1 include: KCAAYCATGGCK (SEQ ID NO:13); KCAAHCATGGCK (SEQ ID NO:14); KCAAYCATGGCKNNC (SEQ ID NO:15); KCAAHCATGGCKNNC (SEQ ID NO:16); and CRYCGCAACCATGGCKGYCG (SEQ ID NO:17), where 'K' indicates the nucleotide can be G or T, 'Y' indicates the nucleotide can be C or T, 'H' indicates the nucleotide can be A, C, or T, and 'R' indicates the nucleotide can be A or G. It is to be understood that sequences provided herein correspond to nucleotides used in DNA molecules and constructs, and where the sequence can be interpreted to be part of an RNA molecule, the nucleotide uracil or 'U' replaces thymidine or 'T'.

TABLE 1

Consensus Kozak Sequences

| SEQ ID NO: | SEQUENCE | DESCRIPTION |
|---|---|---|
| 1 | GCAACC<u>ATG</u>GCT | *Nannochloropsis* Kozak sequence |
| 2 | GCAATC<u>ATG</u>GCT | Variant at position −2 (T) |

TABLE 1 -continued

Consensus Kozak Sequences

| SEQ ID NO: | SEQUENCE | DESCRIPTION |
|---|---|---|
| 3 | GCAACCATGGCG | Variant at position +6 |
| 4 | GCAATCATGGCG | Variant at positions -2 (T) and +6 |
| 5 | TCAACCATGGCT | Variant at position -6 |
| 6 | TCAATCATGGCT | Variant at positions -6 and -2 |
| 7 | TCAACCATGGCG | Variant at positions -6 and +6 |
| 8 | TCAATCATGGCG | Variant at positions -6, -2 (T), and +6 |
| 9 | GCAAACATGGCT | Variant at position -2 (A) |
| 10 | GCAAACATGGCG | Variant at positions -2 (A) and +6 |
| 11 | TCAAACATGGCT | Variant at positions -6 and -2 (A) |
| 12 | TCAAACATGGCG | Variant at positions -6, -2 (A), and +6 |
| 13 | KCAAYCATGGCK | Kozak consensus sequence |
| 14 | KCAAHCATGGCK | Kozak consensus sequence |
| 15 | KCAAYCATGGCKNNC | Kozak consensus sequence |
| 16 | KCAAHCATGGCKNNC | Kozak consensus sequence |
| 17 | CRYCGCAACCATGGCKGYCG | Extended Kozak consensus sequence |
| 18 | CACCGCAACCATGGCGGCCG | Extended *Nannochloropsis* Kozak sequence |
| 19 | CCTCGCAACCATGGCTGTCG | Extended *Nannochloropsis* Kozak sequence |
| 20 | CCTCGCAACCATGGCTGCCG | Extended *Nannochloropsis* Kozak sequence |

For example, a recombinant DNA molecule as provided herein can include a Kozak sequence that conforms to any of the possible combinations provided by SEQ ID NO:13, SEQ ID NO:14, SEQ ID NO:15, SEQ ID NO:16, or SEQ ID NO:17, including, as nonlimiting examples, any of: a nucleotide sequence consisting of the sequence of SEQ ID NO:1; a nucleotide sequence consisting of the sequence of SEQ ID NO:2; a nucleotide sequence consisting of the sequence of SEQ ID NO:3; a nucleotide sequence consisting of the sequence of SEQ ID NO:4; a nucleotide sequence consisting of the sequence of SEQ ID NO:5; a nucleotide sequence consisting of the sequence of SEQ ID NO:6; a nucleotide sequence consisting of the sequence of SEQ ID NO:7; a nucleotide sequence consisting of the sequence of SEQ ID NO:8; a nucleotide sequence consisting of the sequence of SEQ ID NO:9; a nucleotide sequence consisting of the sequence of SEQ ID NO:10; a nucleotide sequence consisting of the sequence of SEQ ID NO:11; a nucleotide sequence consisting of the sequence of SEQ ID NO:12; a nucleotide sequence consisting of the sequence of SEQ ID NO:18; a nucleotide sequence consisting of the sequence of SEQ ID NO:19; and a nucleotide sequence consisting of the sequence of SEQ ID NO:20. The recombinant DNA molecule that includes a Kozak sequence as provided herein further includes a sequence encoding a polypeptide, in which the Kozak sequence is heterologous with respect to the polypeptide-encoding sequence, and the A, T, and G of the initiating methionine codon of the polypeptide-encoding sequence are positions 1, 2, and 3 of the heterologous Kozak sequence (using the numbering system provided in Tables 2 and 3).

The Kozak sequence, when operably linked to a heterologous polypeptide-encoding sequence, can increase translational efficiency of the RNA resulting from transcription of the polypeptide-encoding sequence. For example, the use of a Kozak sequence as provided herein operably linked to a nucleotide sequence encoding a protein of interest can increase the abundance of the protein in a cell in which the nucleotide sequence is expressed. Methods for assessing the strength of a Kozak sequence are well-known in the art, and can include but are not limited to determining protein abundance, for example, by immunological detection or mass spectrometry, or by in vivo assays using a reporter gene, such as a fluorescent protein gene. Testing of sequence modifications, including deletions and base substitutions of the Kozak sequences using reporter constructs, are well-known in the art.

C. Expression Constructs

Expression constructs are also provided herein, in which an expression construct comprises one or more promoters, wherein a promoter is operably linked upstream to a heterologous Kozak sequence as provided herein. An expression construct as provided herein can comprise a promoter operably linked upstream of an isolated nucleic acid molecule that conforms to any of the possible sequence combinations provided by SEQ ID NO:13, SEQ ID NO:14, SEQ ID NO:15, SEQ ID NO:16, or SEQ ID NO:17, including, as nonlimiting examples, any of SEQ ID NOs:1-12 and 18-20. The basic techniques for operably linking two or more sequences of DNA together are familiar to the skilled worker, and such methods have been described in a number of texts for standard molecular biological manipulation (see, e.g., "*Molecular Cloning: A Laboratory Manual,*" 2$^{nd}$ ed. Cold Spring Harbor Laboratory Press, Cold Spring Harbor, N.Y.; Gibson et al. (2009) *Nature Methods* 6:343-45). A promoter can be separated from the Kozak sequence by from 1-10, 10-20, 20-30, 30-40, 40-50, 50-60, 60-70, 70-80, 80-90, 90-100, 100-150, 150-200, 200-250, 250-300, 300-350, 350-400, 400-500, 500-1000, 1000-1500, or greater than 1500 nucleotides. For example, a promoter can include sequences upstream of a transcriptional start site and optionally may include sequences downstream of a transcriptional start site. Sequences from the transcriptional start site to the translational start site are referred to as the 5' untranslated region of the gene or transcript. The construct can include a 5' UTR (which extends into the Kozak sequence), which may be homologous or heterologous with respect to the protein-encoding nucleotide sequence, that may be, for example, 1-10, 10-20, 20-30, 30-40, 40-50, 50-60, 60-70, 70-80, 80-90, 90-100, 100-150, 150-200, 200-250, 250-300, 300-350, 350-400, 400-500, 500-1000, 1000-1500, or greater than 1500 nucleotides in length. For example, the 5' UTR of an expression construct that includes a promoter operably linked to a heterologous Kozak sequence can be from 10 to 300 nucleotides in length, for example, from 20 to 200 nucleotides in length.

The expression constructs of the present invention can comprise any suitable promoter capable of driving transcription in a host organism. Any known or later-discovered promoter sequence can be operably linked into an expression construct of the present invention using known methods. Non-limiting examples of known promoters suitable for use include: a simian vacuolating virus 40 (SV40) promoter; a cauliflower mosaic virus (CaMV) promoter; a cytomegalovirus (CMV) promoter; an actin promoter; a glyceraldehyde 3-phosphate dehydrogenase (GAPDH) promoter; an oxygen evolving enhancer protein 1 (OEE1) promoter; an oxygen evolving enhancer protein 3 (OEE3) promoter; a photosystem II, reaction center W (PSiiW) promoter; a 40S ribosomal protein S12 promoter; and a photosystem I, light harvesting complex (PSI-LHC) promoter. The promoter can be a promoter derived from a heterokont or a green alga, for example, such as the vcp promoter disclosed in US 2009/0317904 or the bidirectional promoters disclosed in US 2010/0210832. Promoters specific to *Nannochloropsis* that could be of particular use in the present invention are disclosed in co-pending U.S. patent application Ser. No. 13/486,930, entitled "Promoters and Terminators for Use in Eukaryotic Cells" filed on 1 Jun. 2012, which is incorporated herein by reference in its entirety.

The expression constructs as provided herein can be made part of a cloning vector and/or an expression vector for transfection into a host cell.

D. Expression Cassettes

Expression cassettes are also provided in which the expression cassettes comprise an expression construct as provided herein, operably linked to a gene of interest. These expression cassettes comprise isolated nucleic acid molecules that include any one of the expression constructs described herein, operably linked to a gene of interest, with the gene of interest positioned such that the adenine of the gene of interest's start codon occupies position +1 of the expression construct's heterologous Kozak sequence. The expression cassettes provided herein may optionally include a terminator sequence or combination of terminator sequences linked downstream of the transgene of interest. The basic techniques for operably linking two or more sequences of DNA together are familiar to the skilled worker, and such methods have been described in a number of texts for standard molecular biological manipulation (see, e.g., "*Molecular Cloning: A Laboratory Manual,*" 2$^{nd}$ ed. Cold Spring Harbor Laboratory Press, Cold Spring Harbor, N.Y.; Gibson et al. (2009) *Nature Methods* 6:343-45).

The expression cassettes, as provided herein, by virtue of comprising the expression constructs as provided herein, necessarily comprise a heterologous Kozak sequence as provided herein. The expression cassettes of the present invention can be used with any gene, e.g. a homologous or heterologous gene. Any known or later-discovered gene can be operably linked to a heterologous Kozak sequence of the invention using known methods. Non-limiting examples of known genes suitable for use with the heterologous Kozak sequences of the invention include genes encoding: proteins associated with lipid biosynthesis; proteins having lipolytic activity; proteins associated with carbohydrate metabolism; transporter polypeptides; proteins conferring resistance to an antibiotic, herbicide, or toxin; reporter proteins (e.g., fluorescent proteins or enzymes that produce detectable products); polypeptides of the Calvin-Benson cycle; polypeptides that participate in photosynthesis (such as but not limited to, photosynthetic reaction center polypeptides, light-harvesting chlorophyll-binding proteins, oxygen-evolving complex polypeptides, cytochromes, ferredoxins, etc.); dehydrogenases, such as NADPH-forming dehydrogenases; transcription factors; or proteins involved in cell signaling (e.g., G proteins or kinases). Further, the gene can be codon optimized for expression in a particular host cell, such as an algal or heterokont species.

The expression cassettes of the present invention can comprise any suitable promoter capable of driving transcription in a host organism. Any known or later-discovered promoter sequences can be operably linked into an expression cassette of the present invention using known methods. Non-limiting examples of known promoters suitable for use include: a SV40 promoter; a CaMV promoter; a CMV promoter; an actin promoter; a GAPDH promoter; an OEE1 promoter; an OEE3 promoter; a PSiiW promoter; a 40S ribosomal protein S12 promoter; and a PSI-LHC promoter. The promoter can be a promoter derived from a heterokont or a green alga. Promoters specific to *Nannochloropsis* that could be of particular use in the present invention are disclosed in co-pending U.S. patent application Ser. No. 13/486,930, entitled "Promoters and Terminators for Use in Eukaryotic Cells" filed on 1 Jun. 2012. The promoter for use in the expression cassettes of the present invention can be a promoter that is active in a heterokont or a eukaryotic microalga. The expression cassette may optionally include a transit peptide-encoding sequence for directing the expressed enzyme to the chloroplast or endoplasmic reticulum of transformed eukaryotic cells, an intron sequence, a sequence having a poly-adenylation signal, etc.

E. Vectors

The present invention also provides vectors that comprise the expression constructs and/or expression cassettes described herein. A vector that includes a Kozak sequence as provided herein may be a cloning vector or an expression vector. For example, a vector that includes a Kozak sequence as provided herein can include either or both of a eukaryotic promoter positioned upstream of the Kozak sequence, or a polypeptide-encoding nucleotide sequence operably linked to the Kozak sequence, such that the initiating methionine codon of the polypeptide-encoding nucleotide sequence consists of the nucleotides A, T, and G that are positions 1, 2, and 3 of the Kozak sequence (numbering as in Table 2 and Table 3). The Kozak sequence can for example, be any Kozak sequence that conforms to the consensus sequences KCAAYCATGGCK (SEQ ID NO:13); KCAAHCATGGCK (SEQ ID NO:14); KCAAYCATGGCKNNC (SEQ ID NO:15); KCAAHCATGGCKNNC (SEQ ID NO:16); and CRYCGCAACCATGGCKGYCG (SEQ ID NO:17), and can comprise, in non-limiting examples, any of SEQ ID NO:1, 2, 3, 4, 5, 6, 7, 8, 9, 10, 11, 12, 18, 19, or 20. The vectors comprise the expression constructs and/or the expression cassettes described herein and can further include at least one origin of replication ("ORI") sequence for replication in a cell. The vectors may further optionally comprise one or more selectable markers under the control of one or more eukaryotic promoters, one or more selectable markers under the control of one or more prokaryotic promoters, and/or one or more sequences that mediate recombination of an exogenous nucleic acid sequence into the target cell's genome.

An ORI is the sequence in a DNA molecule at which replication begins. The ORI serves as a base of assembly for the pre-replication complex. Depending on the ORI, such replication can proceed unidirectionally or bidirectionally. An expression vector as provided herein can include an ORI for replication of the expression vector in a cloning host, such as E. coli or Saccharomyces, and/or can include an ORI for replication of the expression vector in a target cell, which can be, for example, an algal or heterokont cell. The structural biology of ORIs is widely conserved among prokaryotes, eukaryotes, and viruses. Most ORIs possess simple tri-, tetra-, or higher nucleotide repetition patterns. Most are AT-rich and contain inverted repeats. Those skilled in the art will be familiar with the more common ORIs, such as the p15A ORI and the pUC ORI.

A vector may also carry a selectable marker. By way of example, a vector that includes an expression cassette may include, as a selectable marker, a gene conferring resistance to a poison, such as an antibiotic, a herbicide, or some other toxin, so that transformants can be selected by exposing the cells to the poison and selecting those cells which survive the encounter. Non-limiting examples of selectable markers include:

a gene conferring resistance to antibiotics such as amikacin (aphA6), ampicillin (amp$^R$), blasticidin (bls, bsr, bsd), bleomicin or phleomycin (ZEOCIN™) (ble), chloramphenicol (cat), emetine (RBS 14p or cry1-1), erythromycin (ermE), G418 (GENETICIN™) (neo), gentamycin (aac3 or aacC4), hygromycin B (aphIV, hph, hpt), kanamycin (val), methotrexate (DHFR mtx$^R$), penicillin and other β-lactams (β-lactamases), streptomycin or spectinomycin (aadA, spec/strep), and tetracycline (tetA, tetM, tetQ);

a gene conferring tolerance to herbicides such as aminotriazole, amitrole, andrimid, aryloxyphenoxy propionates, atrazines (psbA), bipyridyliums, bromoxynil, cyclohexandione oximes, dalapon, dicamba, diclfop, dichlorophenyl dimethyl urea (DCMU), difunone, diketonitriles, diuron, fluridone, glufosinate, glyphosate, halogenated hydrobenzonitriles, haloxyfop, 4-hydroxypyridines, imidazolinones, isoxasflutole, isoxazoles, isoxazolidinones, miroamide B, p-nitrodiphenylethers, norflurazon, oxadiazoles, m-phenoxybenzamides, N-phenyl imides, pinoxadin, protoporphyrionogen oxidase inhibitors, pyridazinones, pyrazolinates, sulfonylureas, 1,2,4-triazol pyrimidine, triketones, or urea compounds; herbicide tolerance genes such as acetyl CoA carboxylase (ACCase), acetohydroxy acid synthase (ahas), acetolactate synthase (als, csr1-1, csr1-2, imr1, imr2), aminoglycoside phosphotransferase (apt), anthranilate synthase, bromoxynil nitrilase (bxn), cytochrome P450-NADH-cytochrome P450 oxidoreductase, dalapon dehalogenase (dehal), dihydropteroate synthase (sul), class I 5-enolpyruvylshikimate-3-phosphate synthase (EPSPS), class II EPSPS (aroA), non-class I/II EPSPS, glutathione reductase, glyphosate acetyltransferase (gat), glyphosate oxidoreductase (gox), hydroxyphenylpyruvate dehydrogenase, hydroxy-phenylpyruvate dioxygenase (hppd), isoprenyl pyrophosphate isomerase, lycopene cyclase, phosphinothricin acetyl transferase (pat, bar), phytoene desaturase (cal), prenyl transferase, protoporphyrin oxidase, psbA of photosystem II (psbA), and SMM esterase (SulE) superoxide dismutase (sod);

a gene that may be used in auxotrophic strains or to confer autotrophic growth or other metabolic effects, such as arg7, his3, hisD, hisG, lysA, manA, metE, nit1, trpB, ura3, xylA, a dihydrofolate reductase gene, a mannose-6-phosphate isomerase gene, a nitrate reductase gene, or an ornithine decarboxylase gene; a negative selection factor such as thymidine kinase; or toxin resistance factors such as a 2-deoxyglucose resistance gene.

The selectable marker gene can be operably linked to a promoter and under the control of a promoter. The promoter regulating expression of the selectable marker may be conditional or inducible but is preferably constitutive, and can be, for example, any promoter described herein or another promoter. Alternatively, the selectable marker may be placed under the control of the expression cassette promoter. If a selectable marker is placed under the control of the expression cassette promoter, the selectable marker and the expression cassette may be operably linked with an internal ribosome entry site ("IRES") element between the expression cassette and the selectable marker (Komar & Hatzoglou (2011) Cell Cycle 10:229-40 and Hellen & Sarnow (2001) Genes & Dev. 15:1593-612, incorporated by reference in their entireties) or a "2A" sequence (Kim et al. (2011) PLoS One 6(4):e18556, incorporated by reference in its entirety).

Further provided herein is a vector for transformation of a eukaryotic cell, such as but not limited to a eukaryotic microalgal cell or heterokont cell, in which the vector includes a selectable marker gene operably linked to a promoter. The expression or transformation vector can further include one or more additional genes or constructs for transfer into the host cell, such as a gene encoding a polypeptide, such as but not limited to any described hereinabove, where the gene encoding a polypeptide can optionally be operably linked to a promoter as described hereinabove, or can optionally be operably linked to another promoter.

In an alternative transformation strategy, a selectable marker operably linked to a promoter such as a promoter described hereinabove can be provided on a separate construct, where both the gene-of-interest construct and the selectable marker construct are used together in transformation protocols. Selected transformants are then analyzed for co-transformation of the construct that includes the gene-of-interest (see, e.g., Kindle (1990) Proc. Nat'l. Acad. Sci. USA 87:1228-32).

If a vector as provided herein includes an expression cassette but lacks a selectable marker gene, transformants may be selected by routine methods familiar to those skilled in the art, such as, by way of a non-limiting example, extracting nucleic acid from the putative transformants and screening by PCR.

Additionally or alternatively, transformants may be screened by detecting expression of a reporter gene such as, but not limited to, a chloramphenicol acyltransferase gene (cat), lacZ, uidA, xylE, an alkaline phosphatase gene, an α-amylase gene, an α-galactosidase gene, a β-lactamase gene, a β-glucuronidase gene, a horseradish peroxidase gene, a luciferin/luciferase gene, an R-locus gene, a tyrosinase gene, or a gene encoding a fluorescent protein, such as any of the blue, cyan, green, red, yellow, photoconvertible, or photoswitchable fluorescent proteins or any of their variants, including codon-optimized, rapidly folding, monomeric, increased stability, and enhanced fluorescence variants. An expression or transformation vector may include a gene encoding a reporter protein, such as, for example, a fluorescent protein, operably linked to a promoter.

Additionally or alternatively, the vector is designed for integration of one or more genes (such as the expression cassette) into the host genome. For example, the expression or transformation vectors may include *Agrobacterium* flanking sequences designed for integrating transgenes into the genome of a target plant cell. Additionally or alternatively, vectors can be targeted for integration into a plant or algal chromosome by including flanking sequences that enable homologous recombination into the chromosome or targeted for integration into endogenous host plasmids by including flanking sequences that enable homologous recombination into the endogenous plasmids. In some cases in which it may be advantageous to transform the chloroplast of a higher plant or alga, the expression or transformation vectors can be designed to have regions of sequences flanking the transgene that are homologous to chloroplast sequences to promote homologous recombination and integration of the sequence of interest. Further, an expression or transformation vector can include sequences for site-specific recombination such as but not limited to lox sites on which the Cre recombinase acts.

In addition to the promoters described above, one skilled in the art would know various promoters, introns, enhancers, transit peptides, targeting signal sequences, 5' and 3' untranslated regions (UTRs), IRES, 2A sequences, and terminator sequences, as well as other molecules involved in the regulation of gene expression that are useful in the design of effective expression or transformation vectors. In some examples, the expression or transformation vector will contain one or more enhancer elements. Enhancers are short regions of DNA that can bind trans-acting factors to enhance transcription levels. Although enhancers usually act in cis, an enhancer need not be particularly close to its target gene, and may sometimes not be located on the same chromosome. Enhancers can sometimes be located in introns.

Additionally or alternatively, a gene or genes encoding enzymes that participate in the synthesis of a fatty acid product (e.g., a fatty acid, a fatty acid derivative, or a glycerolipid) can be cloned into an expression vector as an expression cassette that includes a heterologous Kozak sequence as disclosed herein. The expression cassette may optionally include a transit peptide-encoding sequence for directing the expressed enzyme to the chloroplast or endoplasmic reticulum of transformed eukaryotic cells, an intron sequence, a sequence having a poly-adenylation signal, etc.

Additionally or alternatively, an expression vector is provided comprising an expression cassette as described herein, wherein the expression vector further comprises one or more of: a selectable marker gene, an origin of replication, and one or more sequences for promoting integration of the expression cassette into the host genome.

Additionally or alternatively, a vector is provided comprising an isolated or recombinant nucleic acid molecule as described herein, wherein the isolated nucleic acid molecule is operably linked to a nucleic acid sequence encoding a selectable marker or a reporter protein, such as, for example, any described herein. Additionally or alternatively, the vector further comprises one or more of: an origin of replication, one or more sequences for promoting integration of the expression cassette into the host genome, a sequence as reported herein that comprises a terminator, or an additional gene, wherein the additional gene encodes an antisense RNA, a microRNA, an shRNA, a ribozyme, structural protein, an enzyme, a transcription factor, or a transporter.

F. Transformation Methods

The present invention provides transformation methods in which a eukaryotic cell is transformed with an expression vector as described herein. The methods comprise introducing an expression vector as provided herein that includes a heterologous Kozak sequence as disclosed herein into a host cell and then selecting for a transformant. The expression vector may be introduced by many methods familiar to those skilled in the art including, as non-limiting examples: natural DNA uptake (Chung et al. (1998) *FEMS Microbiol. Lett.* 164:353-61; Frigaard et al. (2004) *Methods Mol. Biol.* 274: 325-40; Zang et al. (2007) *J. Microbiol.* 45:241-45), conjugation, transduction, glass bead transformation (Kindle et al. (1989) *J. Cell Biol.* 109:2589-601; Feng et al. (2009) *Mol. Biol. Rep.* 36:1433-39; U.S. Pat. No. 5,661,017), silicon carbide whisker transformation (Dunahay et al. (1997) *Methods Mol. Biol.* 62:503-09), biolistics (Dawson et al. (1997) *Curr. Microbiol.* 3:356-62; Hallmann et al. (1997) *Proc. Nat'l. Acad. USA* 94:7469-74; Jakobiak et al. (2004) *Protist* 155: 381-93; Tan et al. (2005) *J. Microbiol.* 43:361-65; Steinbrenner et al. (2006) *Appl. Environ. Microbiol.* 72:7477-84; Kroth (2007) *Methods Mol. Biol.* 390:257-67; U.S. Pat. No. 5,661, 017) electroporation (Kjaerulff et al. (1994) *Photosynth. Res.* 41:277-83; Iwai et al. (2004) *Plant Cell. Physiol.* 45:171-75; Ravindran et al. (2006) *J. Microbiol. Methods* 66:174-76; Sun et al. (2006) *Gene* 377:140-49; Wang et al. (2007) *Appl. Microbiol. Biotechnol.* 76:651-57; Chaurasia et al. (2008) *J. Microbiol. Methods* 73:133-41; Ludwig et al. (2008) *Appl. Microbiol. Biotechnol.* 78:729-35), laser-mediated transformation, or incubation with DNA in the presence of or after pre-treatment with any of poly(amidoamine) dendrimers (Pasupathy et al. (2008) *Biotechnol. J.* 3:1078-82), polyethylene glycol (Ohnuma et al. (2008) *Plant Cell. Physiol.* 49:117-20), cationic lipids (Muradawa et al. (2008) *J. Biosci. Bioeng.* 105:77-80), dextran, calcium phosphate, or calcium chloride (Mendez-Alvarez et al. (1994) *J. Bacteriol.* 176:7395-97), optionally after treatment of the cells with cell wall-degrading enzymes (Perrone et al. (1998) *Mol. Biol. Cell* 9:3351-65) *Agrobacterium*-mediated transformation can also be performed on algal cells, for example after removing or wounding the algal cell wall (e.g., WO 2000/062601). Biolistic methods have been shown to be successful for transformation of the chloroplasts of plant and eukaryotic algal species (see, e.g., WO 2007/133558, incorporated by reference in its entirety). When transforming chloroplasts, it can be useful to codon-optimize the gene of interest for expression in chloroplasts (see, e.g., WO 2011/034863, incorporated by reference in its entirety).

The eukaryotic cell transformed according to the methods of the present invention can be, for example, a fungal, heterokont, algal, or plant cell. For example, the eukaryotic cell transformed using an expression vector as provided herein can be an algal cell, such as a species of genera *Achnanthes, Amphiprora, Amphora, Ankistrodesmus, Asteromonas,*

*Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella, Vischeria,* or *Volvox.*

For example, the eukaryotic cell transformed using the methods provided herein can optionally be a species of *Nannochloropsis*, such as *Nannochloropsis gaditana, Nannochloropsis granulata, Nannochloropsis limnetica, Nannochloropsis maritima, Nannochloropsis oceanica, Nannochloropsis oculata,* or *Nannochloropsis salina.*

In further examples, the eukaryotic cell can be a heterokont cell, optionally, a species belonging to the order Chytridiomycota or Labyrinthulales, preferably a species of Thraustochytrid, Thraustochytrium, Labrynthula, Labyrinthuloides, Japonochytrium, or Schizochytrium.

In some examples, a *Nannochloropsis* cell is transformed by electroporation or particle bombardment. The expression vector used to transform the host cell may encode for a selectable marker, an antibiotic-resistance conferring peptide, a polypeptide, or a functional RNA.

G. Recombinant Eukaryotic Microorganisms

Recombinant eukaryotic microorganisms, such as any of the cells described hereinabove, transformed with a nucleic acid molecule comprising a heterologous Kozak sequence of the present invention and a gene encoding a protein of interest are also provided herein. A recombinant eukaryotic microorganism of the present invention produces a greater amount of the protein of interest than is produced by a control eukaryotic microorganism substantially identical to the recombinant eukaryotic microorganism of the present invention, except that the control eukaryotic microorganism lacks a heterologous Kozak sequence of the present invention selected from a nucleic acid molecule conforming to any of the consensus sequences provided as SEQ ID NO:13, SEQ ID NO:14, SEQ ID NO:15, SEQ ID NO:16, or SEQ ID NO:17, or any Kozak sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:18, SEQ ID NO:19, and SEQ ID NO:20.

The recombinant eukaryotic microorganisms of the present invention can be grown and cultured to produce transformed eukaryotic cell cultures. These cultures can be diluted, plated on agar, and allowed to grow until isolated colonies can be selected for further propagation as clonal strains.

Therefore, in one aspect a recombinant eukaryotic cell is provided comprising an isolated or recombinant nucleic acid molecule as described herein, or an expression construct as described herein, or an expression cassette as described herein, or an expression vector as described herein.

By way of non-limiting example, the recombinant eukaryotic cell of the present invention can be a fungal, heterokont, algal, or plant cell. For example, the eukaryotic cell transformed using an expression vector as provided herein can be an algal cell, such as a species of genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella, Vischeria,* or *Volvox.*

For example, the eukaryotic cell transformed using the methods provided herein can optionally be a species of *Nannochloropsis*, such as *Nannochloropsis gaditana, Nannochloropsis granulata, Nannochloropsis limnetica, Nannochloropsis maritima, Nannochloropsis oceanica, Nannochloropsis oculata,* or *Nannochloropsis salina.*

In further examples, the eukaryotic cell can be a heterokont cell, optionally, a species belonging to the order Chytridiomycota or Labyrinthulales, preferably a species of Thraustochytrid, Thraustochytrium, Labrynthula, Labyrinthuloides, Japonochytrium, or Schizochytrium.

Algae can be cultured phototrophically, in the absence of a fixed carbon source, or mixotrophically, where the cultures are supplied with light for at least part of the day, and also supplied with a reduced carbon source, such as a sugar (e.g., glucose, fructose, galactose, mannose, rhamnose, arabinose, xylose, lactose, sucrose, maltose), an organic acid (e.g., acetate, citrate, succinate), or glycerol. A recombinant photosynthetic eukaryotic microorganism in some embodiments is cultured mixotrophically, in which the organism is grown in the presence of light for at least a part of the day, and also provided with one or more sources of reduced carbon. A photosynthetic organism can be grown mixotrophically for a period of time, followed by a period of phototrophic growth, or vice versa.

Media for phototrophic or mixotrophic growth of algae are known in the art, and media can be optimized to enhance growth or production of fatty acid products for a particular species. Artificial light sources can be used as the sole light source or to enhance or extend natural light.

Growth of algae can be in open areas, such as, for example, ponds, canals, channels, raceways, or tanks, or can be in bioreactors. Bioreactors are preferred for mixotrophic growth, and can also be used for phototrophic growth. The bioreactors can be of any sizes and form, and can include inlets for providing nutrients, additives, or gases, such as but not limited to air or $CO_2$. A bioreactor preferably also has an outlet for sampling of the culture. A bioreactor can be configured such that the algal culture is mixed during the growth period, for example, by stirring, rocking, shaking, inverting, bubbling of gases through the culture, etc. Outdoor ponds, raceways, tanks, canals, etc. can also be designed for mixing of cultures through, for example, paddles, pumps, hoses or jets for circulation of the culture media, or tubes, hoses or inlets for supplying air or $CO_2$ to the culture.

H. Protein Expression Methods

Methods for expressing a protein of interest are also provided, comprising (1) transforming a eukaryotic cell with an expression vector comprising an expression cassette according to the present invention and (2) culturing the transformed cell under conditions such that the protein of interest is expressed.

In particular aspects, the transformed eukaryotic cell used for expressing a protein of interest can be a fungal, heterokont, algal, or plant cell. For example, the eukaryotic cell transformed using an expression vector as provided herein can be an algal cell, such as a species of genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella, Vischeria,* or *Volvox*.

For example, the eukaryotic cell transformed using the methods provided herein can optionally be a species of *Nannochloropsis*, such as *Nannochloropsis gaditana, Nannochloropsis granulata, Nannochloropsis limnetica, Nannochloropsis maritima, Nannochloropsis oceanica, Nannochloropsis oculata,* or *Nannochloropsis salina*.

Culturing can make use of solid or liquid growth media. Recipes and formulations for making growth media are generally available from a wide variety of sources, as are instructions for the preparation of particular media suitable for a wide variety of strains of microorganisms. For example, for algae, various fresh water and salt water media can include those described in Barsanti (2005) Algae: Anatomy, Biochemistry & Biotechnology, CRC Press for media and methods for culturing algae. Algal media recipes can also be found at the websites of various algal culture collections, including, as nonlimiting examples, the UTEX Culture Collection of Algae (www.sbs.utexas.edu/utex/media.aspx) (visited 15 Nov. 2012); Culture Collection of Algae and Protozoa (www.ccap.ac.uk) (visited 15 Nov. 2012); and CAUP Culture Collection (botany.natur.cuni.cz/algo/caup-media.html) (visited 15 Nov. 2012).

In some embodiments, the nitrogen content of the medium can be "replete", that is, the level of nitrogen is not limiting to culture propagation. The amount of nitrogen required in a replete nitrogen culture medium can vary depending on the algal strain and other culture conditions, but preferably is at least about 250 µM, at least 500 µM, or at least 800 µM, such as at least 1 mM, at least 2 mM, at least 3 mM, at least 4 mM, at least 5 mM, at least 6 mM, at least 7 mM, or at least 8 mM nitrogen, which is preferably supplied as ammonia and/or nitrate, but can be supplied as any utilizable nitrogen source compound. In some embodiments, the culture medium can be nitrogen replete and can lack a supplementary organic carbon source. In some embodiments, the culture medium can be nutrient replete, where no nutrients (not including a carbon source) are limiting for culture propagation, and the culture medium can lack a supplementary organic carbon source.

The culture methods can optionally include inducing expression of a the gene that is operably linked to the heterologous Kozak sequence as provided herein. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the promoter operably linked to the gene of interest.

In some embodiments of the present invention, the recombinant microorganisms or host cells can be cultured in a bioreactor. "Bioreactor" refers to an enclosure or partial enclosure in which cells are cultured, optionally in suspension and, when suspended, preferably in an aqueous liquid. The bioreactor can be used to culture microalgal cells through the various phases of their physiological cycle. Bioreactors can offer many advantages for use in heterotrophic growth and propagation methods. To produce biomass for use as food, microorganisms or host cells are preferably fermented in large quantities in liquid, such as in suspension cultures as an example. Bioreactors such as steel fermentors can accommodate very large culture volumes (40,000 liter and greater capacity bioreactors can be used in various embodiments of the invention). Bioreactors can also typically allow for the control of one or more culture conditions such as temperature, pH, oxygen tension, carbon dioxide levels, and the like, as well as combinations thereof. Bioreactors can typically be configurable, for example, using ports attached to tubing, to allow gaseous components, such as $CO_2$, $CO_2$-enriched air, oxygen, and/or nitrogen, to be contacted with (e.g., bubbled through) a liquid culture. Other culture parameters, such as the pH of the culture media, the identity and/or concentration of trace elements and/or nutrients, the identity and/or concentration of other media constituents, or the like, or combinations thereof, can typically be more readily manipulated using a bioreactor.

Photosynthetic microorganisms and host cells (e.g., microalgae) can additionally or alternately be cultured in a bioreactor equipped with an artificial light source, a "photobioreactor", and/or can have one or more walls that is transparent enough to light, including sunlight, to enable, facilitate, and/or maintain acceptable microorganism growth. Algae or other photosynthetic host cells can additionally or alternately be cultured in shake flasks, test tubes, vials, microtiter dishes, petri dishes, or the like, or combinations thereof.

Additionally or alternatively, algae may be grown in ponds, canals, sea-based growth containers, trenches, raceways, channels, or the like, or combinations thereof. As with standard bioreactors, a source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain CO in addition to $CO_2$, it may be necessary to pre-treat such sources such that the CO level introduced into the (photo)bioreactor do not constitute a dangerous and/or lethal dose with respect to the growth and/or survival of the microorganisms.

The protein expressed in the methods of the present invention can be for example: a protein associated with lipid biosynthesis; a protein having lipolytic activity; a protein that participates in photosynthesis; a protein associated with carbon fixation; a transporter protein; a dehydrogenase; a transcription factor; or a cell signaling protein. The protein expressed in the methods of the present invention can be, for example, a chloroplastic protein, a cytoplasmic protein, a nuclear protein, a secreted protein, or a cell-surface protein.

The expression level of the protein of interest according to the methods of the present invention can be enhanced relative to the expression level of the same protein of interest in a control eukaryotic cell, wherein the control eukaryotic cell is substantially identical to the recombinant eukaryotic cell of the present invention, except that the control eukaryotic cell lacks a heterologous Kozak sequence selected from a nucleic acid molecule conforming to any of the consensus sequences provided as SEQ ID NO:13, SEQ ID NO:14, SEQ ID NO:15, SEQ ID NO:16, or SEQ ID NO:17, or any Kozak sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:18, SEQ ID NO:19, and SEQ ID NO:20.

For example, the expression level of the protein of interest can be enhanced at least 5% relative to the expression level from a control eukaryotic cell. Additionally or alternatively, the level of expression of the protein of interest can be enhanced at least 10% relative to expression level from a control eukaryotic cell. Further additionally or alternatively, the level of expression of the protein of interest can be enhanced at least 20% relative to expression level from a control eukaryotic cell. Further additionally or alternatively, the level of expression of the protein of interest can be enhanced at least 30% relative to expression level from a control eukaryotic cell. Further additionally or alternatively, the level of expression of the protein of interest can be enhanced at least 40% relative to expression level from a control eukaryotic cell. Further additionally or alternatively, the level of expression of the protein of interest can be enhanced at least 50% relative to expression level from a control eukaryotic cell. Further additionally or alternatively, the level of expression of the protein of interest can be enhanced at least 60% relative to expression level from a control eukaryotic cell. Further additionally or alternatively, the level of expression of the protein of interest can be enhanced at least 70% relative to expression level from a control eukaryotic cell. Further additionally or alternatively, the level of expression of the protein of interest can be enhanced at least 80% relative to expression level from a control eukaryotic cell. Further additionally or alternatively, the level of expression of the protein of interest can be enhanced at least 90% relative to expression level from a control eukaryotic cell. Further additionally or alternatively, the level of expression of the protein of interest can be enhanced at least 200% relative to expression level from a control eukaryotic cell. Further additionally or alternatively, the level of expression of the protein of interest can be enhanced at least 500% relative to expression level from a control eukaryotic cell. Further additionally or alternatively, the level of expression of the protein of interest can be enhanced at least 1000% relative to expression level from a control eukaryotic cell.

The methods described herein can be used in any eukaryotic species, such as any described herein, and can, for example, be used in a heterokont species as described herein. For example, the methods can be used to enhance expression of a protein of interest in a *Nannochloropsis* species.

I. Further Embodiments

Embodiment 1. A recombinant DNA molecule comprising a Kozak sequence according to any of SEQ ID NO:13, SEQ ID NO:14, SEQ ID NO:15, SEQ ID NO:16, or SEQ ID NO:17 operably linked to at least one of:

a polypeptide-encoding sequence, wherein the Kozak sequence is heterologous with respect to the polypeptide-encoding sequence, and a eukaryotic promoter, wherein the Kozak sequence is heterologous with respect to the promoter; and optionally wherein the Kozak sequence is selected from the group consisting of SEQ ID NOs:1, 2, 3, 4, 5, 6, 7, 8, 9, 10, 11, 12, 18, 19, and 20.

Embodiment 2. A recombinant DNA molecule of Embodiment 1, wherein the polypeptide-encoding sequence is codon optimized for expression in an algal or heterokont species.

Embodiment 3. An expression cassette comprising a gene encoding a polypeptide operably linked to a eukaryotic promoter and to a heterologous Kozak sequence, wherein the ATG codon of the heterologous Kozak sequence is the initiating methionine codon of the gene; and optionally wherein the Kozak sequence is selected from the group consisting of SEQ ID NO:13, SEQ ID NO:14, SEQ ID NO:15, SEQ ID NO:16, or SEQ ID NO:17; further optionally wherein the Kozak sequence is selected from the group consisting of SEQ ID NOs:1, 2, 3, 4, 5, 6, 7, 8, 9, 10, 11, 12, 18, 19, and 20.

Embodiment 4. An expression cassette of Embodiment 3, wherein the eukaryotic promoter is active in a heterokont or eukaryotic microalga, wherein the eukaryotic promoter is a simian vacuolating virus (SV40) promoter, a cauliflower mosaic virus (CaMV) promoter, a cytomegalovirus (CMV) promoter, a promoter derived from a heterokont species, or a promoter derived from a green algal species, and/or wherein the eukaryotic promoter is optionally a *Nannochloropsis* promoter.

Embodiment 5. A vector comprising a recombinant DNA molecule according to Embodiment 1, wherein the vector optionally comprises one or more of: a selectable marker; an origin of replication functional in an algal or heterokont cell; and recombination sequences.

Embodiment 6. A method for transforming a eukaryotic cell comprising:

introducing a vector according to Embodiment 5 into the eukaryotic cell; and selecting for a transformed eukaryotic cell.

Embodiment 7. A recombinant eukaryotic microorganism comprising: a recombinant nucleic acid molecule according to Embodiment 1 or Embodiment 2.

Embodiment 8. A recombinant eukaryotic microorganism according to Embodiment 7, wherein the eukaryotic microorganism comprises an expression cassette, and further wherein the recombinant eukaryotic microorganism produces a greater amount of the protein of interest than a control eukaryotic microorganism that is substantially identical to the recombinant eukaryotic microorganism in all material respects except that the control eukaryotic microorganism lacks the heterologous Kozak sequence selected from the group consisting of SEQ ID NOs:1, 2, 3, 4, 5, 6, 7, 8, 9, 10, 11, 12, 18, 19, and 20.

Embodiment 9. A recombinant eukaryotic microorganism according to Embodiment 7 or Embodiment 8, wherein the eukaryotic microorganism is selected from the group consisting of a fungus, a heterokont, an alga, and a plant, wherein the alga is preferably selected from the group consisting of species of the genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetraselmis, Thalassiosira, Tribonema, Vaucheria, Viridiella, Vischeria,* and *Volvox.*

Embodiment 10. A method for expressing a polypeptide of interest in a eukaryotic cell, the method comprising transfecting the eukaryotic cell with a vector comprising the expression cassette of Embodiment 3 and culturing the eukaryotic cell under conditions in which the polypeptide is expressed, optionally wherein the eukaryotic cell is selected from the group consisting of a fungal cell, a heterokont cell, a plant cell, and an algal cell, wherein the algal cell is preferably selected from the group consisting of species of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetraselmis, Thalassiosira, Tribonema, Vaucheria, Viridiella, Vischeria,* and *Volvox.*

Embodiment 10.A method according to Embodiment 9, wherein the protein of interest is (a) a protein associated with lipid biosynthesis, (b) a lipase, (c) a protein that participates in photosynthesis, (d) a protein associated with carbon fixation, (e) a transporter protein, (f) a dehydrogenase, (g) a transcription factor, or (h) a cell signaling protein.

Embodiment 11.The method according to Embodiment 9, wherein expression of the protein of interest is enhanced at least 5%, at least 10%, at least 20%, at least 30%, at least 40%, at least 50%, or at least 60% relative to expression achieved from a substantially identical eukaryotic cell comprising an expression cassette that comprises the gene encoding a polypeptide operably linked to the eukaryotic promoter but lacks the heterologous Kozak sequence.

EXAMPLES

The following examples are merely illustrative, and do not limit this disclosure in any way.

Example 1

Identification of Kozak Sequences

To determine the Kozak sequence for *Nannochloropsis*, transcript profiling was used to determine the frequency of bases at positions immediately downstream and immediately upstream of the "A" of the initiating methionine codon of highly expressed genes. Data from various proprietary *Nannochloropsis* transcriptomics databases were analyzed to provide relative transcription levels for all genes expressed in *Nannochloropsis gaditana*. In general, genes with high levels of expression are correlated with large quantities of protein product, and furthermore tend to possess functional Kozak sequences. Therefore, a rank order was performed on the transcriptome data, bundling the top 100, top 500, and top 1000 most frequently expressed genes in *Nannochloropsis gaditana*. Only genes with no predicted alternate start codons were included in the data sets. The following procedures were used to obtain transcriptome data.

Strains: *Nannochloropsis gaditana* was obtained from the CCMP culture collection (CCMP1894). Cultures were grown for two days in 1 L of nutrient replete medium in 2 L shake flasks at 100 rpm on a 0.75 inch orbital shaker under 160 µE constant light, in the presence of 1% $CO_2$, at 25° C. Light intensity was measured using LI-COR Light Meter, LI-250A. Cell density was measured using an Accuri C6 flow cytometer.

Nutrient replete medium: Medium was prepared by dissolving 35 g of Instant Ocean® (artificial seawater) salts (Aquatic Eco Systems, Apopka, Fla.) in 900 mL of MilliQ filtered water, followed by addition of 7.1 mL of 1 M $NH_4Cl$, 320 µL of 1 M $NaH_2PO_4$, 10 mL of 1 M MOPS pH 8, 1 mL of f/2 Trace Metal Solution (CCMP f/2 Media Kit) and 500 µL of Vitamin Solution CCMP f/2 Media Kit). The solution was brought to 1 L and filter sterilized by passage through a 0.2 micron bottle top filter (Corning #430513). This resulted in a final concentration of 7.1 mM $NH_4Cl$, 320 µM $NaH_2PO_4$, and 10 mM MOPS, with levels of trace metals and vitamins as in f/2 media (Guillard (1975) in: W. L. Smith and M. H. Chanley, eds., Culture of marine invertebrate animals. pp. 29-60, Plenum Book Publ. Corp., New York).

RNA extraction: Cultures were harvested by centrifugation at 4500×g for 5 minutes at 22° C. and supernatant was removed. Glass beads were aliquotted into 2 mL conical tubes with an O-ring (Sorbio 13120) and autoclaved. One cell pellet volume of 500 µm glass beads and two volumes of 40° C. lysis buffer (50 mM Tris-HCl, 20 mM EDTA, 300 mM NaCl, pH 8.0) were added to the cell pellet. Cells were vortexed in a Mini Beadbeater (BioSpec products) for 3×30 seconds, and kept on ice between pulses. A one-tenth volume of 20% SDS was mixed in and tubes were incubated at 50° C. for 30 minutes with several gentle inversions.

The mixture was extracted three times with one volume of phenol/chloroform/isoamyl alcohol until the aqueous phase was clear, saving the supernatant each time. A 2.5× volume of 95% ethanol was added to the supernatant and incubated for 1 hour at −20° C. The nucleic acid was precipitated by centrifugation at 20000×g for 15 minutes, after which the pellet was incubated at 37° C. until dry. The pellet was incubated at 37° C. in 200-500 µL DEPC-treated Milli-Q filtered $H_2O$ until dissolved completely.

To precipitate the RNA, one volume of 4M LiCl (Ambion AM9480) was added to give a final concentration of 2M and the solution was incubated at −20° C. for 2-4 hours then centrifuged at 20000×g for 15 minutes. The supernatant was discarded and the pellet was washed with 1 mL of 70% ethanol and allowed to dry completely. The pellet was incubated at 37° C. in 200-500 µL DEPC-treated Milli-Q filtered H$_2$O until dissolved completely. DNA in the sample was removed by treating the sample using an RNEASY® plant mini kit (Qiagen).

mRNA quality assessment: The mRNA quality was assessed by on-chip gel electrophoresis using an Agilent 2100 Bioanalyzer and RNA6000 LABCHIP® kit according to manufacturer's instructions. RNA quality assessment was guided by an Application Note from the manufacturer.

mRNA sequencing: RNA samples were sequenced by Ambry Genetics (Aliso Viejo, Calif.) after poly-A purification and fragmentation as specified by Illumina (San Diego, Calif.) ("Preparing Samples for Sequencing of mRNA Part #1004898, Rev. A, 2008). mRNA was sequenced using sequencing-by-synthesis (a.k.a. Solexa sequencing) to generate 50 bp singleton reads using the mRNA-Seq procedure (Mortazavi et al., 2008), indexing the nine samples in two lanes of the Illumina Genome Analyzer IIx. Each sample yielded an average of two million mappable reads, which were aligned to the *Nannochloropsis gaditana* reference genome sequence using CLC Genomics Workbench software (CLC-GW; CLC Bio, Denmark). Expression levels were computed for every annotated gene normalized for gene length and total number of mappable reads per sample, and reported in mean reads per kilobase per million mapped reads (RPKM) units for every sample. Mean RPKM is a measure of relative transcriptional levels that normalizes for differences in transcript length (Mortazavi et al., 2008).

Identification of genes: Calculations of expression levels, statistical significance and other metrics were generated using CLC-GW. Specifically, the RNA-Seq Analysis in CLC-GW was used to map the reads in each sample to 10907 annotated genes in proprietary genome and cDNA assemblies of *Nannochloropsis gaditana*. Expression levels in RPKM were calculated for every gene using standard parameters allowing for reads to map up to 50 bp upstream and downstream from every gene.

Identification of a Kozak consensus sequence: Because genes with high levels of expression are correlated with genes that include Kozak sequences, the expression data from the mRNA sequencing was used to rank order the expressed genes to provide the 100 highest expressed and 1000 highest expressed genes in *Nannochloropsis* under nutrient replete conditions. Genes with predicted alternate start positions were excluded from the data set.

Example matrices of: (1) the top 100 genes are provided in Table 2; and (2) the top 1000 genes are provided in Table 3. (For reference, the original elucidation of the vertebrate Kozak sequence analyzed the top approximately 700 expressed genes from various source organisms (Kozak, 1987). In each table, the row label "Pos." in the top row stands for "position relative to the AUG." The row label "Con." in the bottom row stands for "consensus nucleotide sequence."

TABLE 2

% Nucleotide Frequency in 100 most abundant *Nannochloropsis* mRNAs

| Pos. | −10 | −9 | −8 | −7 | −6 | −5 | −4 | −3 | −2 | −1 | 1 | 2 | 3 | 4 | 5 | 6 | 7 | 8 | 9 | 10 |
|---|---|---|---|---|---|---|---|---|---|---|---|---|---|---|---|---|---|---|---|---|
| A | 24 | 24 | 24 | 26 | 21 | 18 | 45 | 65 | 25 | 18 | 100 | 0 | 0 | 24 | 19 | 18 | 31 | 21 | 12 | 22 |
| C | 41 | 32 | 28 | 32 | 16 | 37 | 29 | 6 | 30 | 54 | 0 | 0 | 0 | 20 | 35 | 16 | 17 | 22 | 44 | 17 |
| G | 13 | 17 | 18 | 20 | 33 | 21 | 12 | 19 | 18 | 15 | 0 | 0 | 100 | 40 | 22 | 31 | 33 | 23 | 20 | 41 |
| T | 22 | 27 | 30 | 22 | 30 | 24 | 14 | 10 | 27 | 13 | 0 | 100 | 0 | 16 | 24 | 35 | 19 | 34 | 24 | 20 |
| Con. | C | C | T | C | G | C | A | A | C | C | A | T | G | G | C | T | G | T | C | G |

TABLE 3

% Nucleotide Frequency in 1000 most abundant *Nannochloropsis* mRNAs

| Pos. | −10 | −9 | −8 | −7 | −6 | −5 | −4 | −3 | −2 | −1 | 1 | 2 | 3 | 4 | 5 | 6 | 7 | 8 | 9 | 10 |
|---|---|---|---|---|---|---|---|---|---|---|---|---|---|---|---|---|---|---|---|---|
| A | 26 | 27 | 23 | 24 | 29 | 24 | 37 | 49 | 26 | 21 | 100 | 0 | 0 | 25 | 19 | 19 | 24 | 22 | 21 | 25 |
| C | 31 | 26 | 33 | 27 | 21 | 31 | 26 | 14 | 31 | 44 | 0 | 0 | 0 | 25 | 38 | 29 | 22 | 30 | 34 | 26 |
| G | 21 | 24 | 20 | 26 | 28 | 22 | 20 | 25 | 20 | 18 | 0 | 0 | 100 | 34 | 22 | 27 | 35 | 24 | 24 | 31 |
| T | 22 | 23 | 23 | 23 | 22 | 24 | 18 | 12 | 23 | 16 | 0 | 100 | 0 | 16 | 21 | 25 | 19 | 25 | 22 | 19 |
| Con. | C | A | C | C | A | C | A | A | C | C | A | T | G | G | C | C | G | C | C | G |

Figure 2:
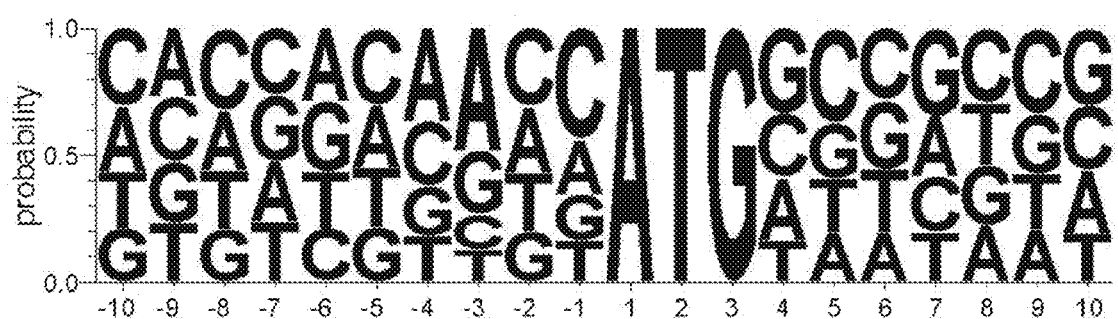
FIG. 2 is a graphical representation of the occupancy percentage of each nucleotide at each position from −10 to +10 around the canonical ATG start codon in the 1000 most abundant *Nannochloropsis* transcripts. The relative size of each letter corresponds to the frequency with which the indicated nucleotide is found in the indicated position in the *Nannochloropsis* 1000 most highly expressed genes of the transcriptome.

FIGS. 1 and 2 are graphical representations, for the top 100 and 1000 genes respectively, of the occupancy percentage of each nucleotide at each position from −10 to +10 with respect to the "A" nucleotide of the canonical ATG at the start of the open reading frame, where the "A" nucleotide of the canonical ATG that encodes the initiating methionine of the encoded protein is designated position +1. One Kozak consensus sequence derived from the frequency data is: (G/T)CAA(C/T)CATGGC(T/G) (SEQ ID NO:13) and another Kozak consensus sequence derived from the data is (G/T)CAAA-CATGGC(G/T) (SEQ ID NO:14). Additional Kozak consensus sequences derived from the data include, for example, (G/T)CAACCATGGC(T/G) (SEQ ID NO:15) and (G/T)CAATCATGGC(T/G) (SEQ ID NO:16).

Individual *Nannochloropsis* Kozak sequences that may be derived from the frequency data include the following: GCAACCATGGCT (SEQ ID NO:1); GCAATCATGGCT (SEQ ID NO:2), GCAACCATGGCG (SEQ ID NO:3), GCAATCATGGCG (SEQ ID NO:4), TCAACCATGGCT (SEQ ID NO:5), TCAATCATGGCT (SEQ ID NO:6), TCAACCATGGCG (SEQ ID NO:7), TCAATCATGGCG (SEQ ID NO:8), GCAAACATGGCT (SEQ ID NO:9), GCAAACATGGCG (SEQ ID NO:10), TCAAACATGGCT (SEQ ID NO:11), and TCAAACATGGCG (SEQ ID NO:12).

The Table 3 matrix containing Top 1000 expressed genes (which includes the top 100 expressed genes) and graphical representation of FIG. 2 show that, while the Kozak signal is still present, the bias is not as extreme as for the Top 100 genes. It is possible that the bias observed in the Top 1000 data set is due to the presence of the Top 100 genes.

Table 4 below lists common Kozak sequences in use and/or under functional analysis. Nucleotides shown in boldface are considered to be the most important for the functioning of the *Nannochloropsis* Kozak sequence. The start codon for each sequence is underlined.

TABLE 4

| Kozak Consensus Sequences | |
|---|---|
| Putative *Nannochloropsis* Kozak | GCAACCATGGCT |
| Higher Plant Conserved Kozak | GTAAAC<u>ATG</u>GCT |
| Vertebrate Related Kozak | GGTACC<u>ATG</u> |

Example 2

Confirmation of the *Nannochloropsis* Kozak Sequence by Proteomic Analysis

To confirm that highly expressed proteins include that identified Kozak consensus sequence, proteins were isolated from a culture of a *Nannochloropsis gaditana* (strain WT-3730), isolated from a culture obtained from the CCMP culture collection (CCMP1894) grown under nutrient replete conditions and proteins having higher than average abundance were identified by mass spectrometry. The protein sequences were used to identify the corresponding genes using proprietary genome and cDNA assemblies, which were in turn used to identify sequences surrounding the initiating methionine of the genes of abundant proteins in order to characterize an algal Kozak sequence.

The *N. gaditana* strain was grown in nutrient replete culture media, and proteins were isolated 48 hours after the onset of the experiment. Three hundred milliliter cultures were grown in 500 mL shake flasks at 125 rpm on an orbital shaker under a (16 h light:8 h dark) diel cycle, using 90-100 μE constant light and 1% $CO_2$ at 25° C. Light intensity was measured using LI-COR Light Meter, LI-250A. Standard nutrient replete media was prepared by dissolving 35 g of Instant Ocean salts (Aquatic Eco Systems, Apopka, Fla.), 5.71 mL of a 1.75 M $NaNO_3$ stock solution, and 5.41 mL of a 77 mM $K_2HPO_4.3H_2O$ stock solution in 981 mL of milliQ filtered water to make 1 liter. The solution was filter sterilized by passage through a 0.2 micron bottle top filter (Corning #430513). On the day of use, a stock vitamin mix and chelated trace metal stock solution was added and the media was mixed by shaking. The vitamin mix included 0.01% thiamine HCl, 0.37 μM cyanocobalamin, and 0.41 μM biotin. The chelated trace metal solution included 11.71 mM disodium EDTA, 11.65 mM $FeCl_3$, 39.2 μM $CuSO_4$, 77.5 μM/$ZnSO_4$, 42 μM $CoCl_2$, 91 μM $MnCl_2$, and 26 μM $Na_2MoO_4$.

After two days (48 hours) of culturing, 50 mLs of algal culture were removed for protein extraction. Cells were pelleted and washed three times with phosphate buffered saline (PBS) after which the final pellets were frozen in liquid nitrogen and stored at −80° C. Protein was extracted from the frozen pellets and trypsin digested, followed by mass spectrometry of isolated proteins.

Mass spectrometry, in combination with proprietary genome and cDNA sequence assemblies, was used to identify high abundance proteins during nutrient replete growth. The nucleotide sequences surrounding the initiating methionine codon of the genes encoding abundant proteins were analyzed to determine the frequency of bases at positions immediately downstream and immediately upstream of the "A" of the initiating methionine codon of highly expressed genes. The proteomic analysis confirmed that the genes identified by transcriptome analysis as being highly expressed (Example 1) were also highly represented in abundant proteins, further supporting the correlation of the identified Kozak consensus with high expression (e.g., translation) of genes in *Nannochloropsis*.

TABLE 5

| % Nucleotide Frequency in 100 most abundant *Nannochloropsis* proteins | | | | | | | | | | | | | | | | | | | | | |
|---|---|---|---|---|---|---|---|---|---|---|---|---|---|---|---|---|---|---|---|---|
| Pos. | −10 | −9 | −8 | −7 | −6 | −5 | −4 | −3 | −2 | −1 | 1 | 2 | 3 | 4 | 5 | 6 | 7 | 8 | 9 | 10 |
| A | 25 | 27 | 22 | 25 | 25 | 27 | 39 | 66 | 26 | 23 | 100 | 0 | 0 | 29 | 22 | 10 | 26 | 14 | 14 | 23 |
| C | 36 | 23 | 36 | 35 | 21 | 36 | 29 | 6 | 40 | 44 | 0 | 0 | 0 | 23 | 46 | 24 | 20 | 44 | 50 | 28 |
| G | 13 | 24 | 16 | 18 | 31 | 17 | 17 | 21 | 20 | 17 | 0 | 0 | 100 | 30 | 14 | 38 | 32 | 20 | 23 | 33 |
| T | 26 | 26 | 26 | 22 | 23 | 20 | 15 | 7 | 14 | 16 | 0 | 100 | 0 | 18 | 18 | 28 | 22 | 22 | 13 | 16 |
| Con. | C | A | C | C | G | C | A | A | C | C | A | T | G | G | C | G | G | C | C | G |

The consensus sequence obtained by comparison of the 100 highest-abundance proteins (Table 5) is highly similar to that of the 100 highest-abundance mRNAs, with only positions −9, −8, +6, and +8 differing in the relative frequency of the nucleotide bases at those positions.

Example 3

Increased Biomolecule Expression

The Kozak sequences of the present invention are used to enhance expression of recombinant proteins in eukaryotic cells, particularly algal cells. Enhanced expression of proteins can, in turn, result in enhanced production of other biomolecules, such as lipids and sugars. A nucleotide sequence chosen from SEQ ID NOs:1-12 is operably linked to a transgene encoding a protein of interest. The transgene is incorporated into a vector for stable expression and transfected into heterokont cells. Individual transformants are selected and grown into pure-strain cultures known as the "experimental strains". At the same time, a transgene encoding the same protein of interest, but lacking the Kozak sequence of the present invention, is expressed in another *N. gaditana* cell (herein "the control strain") under substantially identical culture conditions. The product/protein of interest from these various strains is collected and quantified.

Lipid biosynthesis: In one example, the transgene can encode a diacylglycerol acyltransferase (DGAT). Triacylglyceride per total organic carbon (herein "TAG/TOC") yields from an experimental strain can be 5% higher than yields from the control strain. TAG/TOC yields from an experimental strain may be at least 10% higher than yields from the control strain or may be at least 20% higher than yields from the control strain. TAG/TOC yields from an experimental strain can be, for example, at least 50% higher than yields from the control strain. TAG/TOC yields from an experimental strain may be at least 2-fold the yields from the control strain.

Lipolytic activity: In a second example, the transgene encodes triacylglycerol lipase. Oleic acid per total organic carbon (herein "OA/TOC") yields from an experimental strain can be 5% higher than yields from the control strain. OA/TOC yields from an experimental strain may be at least 10% higher than yields from the control strain and/or OA/TOC yields from an experimental strain may be at least 20% higher than yields from the control strain. OA/TOC yields from an experimental strain can be, for example, at least 50% higher than yields from the control strain, and may be at least 2-fold the yields from the control strain.

Participation in photosynthesis: In a third example, the transgene encodes a variant of a photosynthetic electron transport protein. Oxygen evolution (Pmax) can be at least 5% higher in an experimental strain than in the control strain. For example, Pmax may be at least 10% higher or at least 20% higher in an experimental strain than in the control strain.

Carbon fixation: In a fourth example, the transgene encodes ribulose-1,5-bisphosphate carboxylase oxygenase. Biomass accumulation of a culture of an experimental strain can 5% higher in an experimental strain than in a culture of the control strain cultured for the same amount of time. For example, the rate of biomass accumulation can be at least 10% higher or at least 20% higher in an experimental strain than in the control strain.

Dehydrogenase: In a fifth example, the transgene encodes an NADPH-forming dehydrogenase. Yields of triglyceride per gram of biomass or total organic carbon (TOC) can be at least 5% higher in an experimental strain than in the control strain. Triglyceride per biomass or TOC yields from an experimental strain can be at least 10% higher than yields from the control strain, for example, at least 20% higher than yields from the control strain. Triglyceride per biomass or TOC yields from an experimental strain can be, for example, at least 2-fold yields from the control strain.

Transcription factor: In a sixth example, the transgene encodes a transcription factor (TF). Transcription of a gene (as measured by mRNA yields) regulated by the TF is at least 5% higher in an experimental strain than in the control strain. Transcription of a gene regulated by the TF may be at least 10% higher in an experimental strain and may be at least 20% higher in an experimental strain than in the control strain, for example, at least 2-fold higher in an experimental strain than in the control strain.

A functional *Nannochloropsis* Kozak sequence incorporated into a gene construct can reduce the "translation initiation efficiency" variable from gene expression construct design by consistently maximizing translation of an mRNA. This can allow for maximum production of a protein of interest in *Nannochloropsis* when maximum production is desired, and can also reduce the time needed to develop expression constructs where a specific—but less than maximal—level of protein production is required. In situations where multiple proteins of interest function in a complex requiring a specific protein stoichiometry for proper function, use of a uniform effective Kozak sequence can reduce the variable effects on the final expression of protein products of the ATG surrounding sequence.

Example embodiments are provided so that this disclosure will be thorough, and will fully convey the invention's scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

What is claimed is:

1. A recombinant DNA molecule comprising a Kozak sequence selected from the group consisting of SEQ ID NO:13, SEQ ID NO:14, SEQ ID NO:15, SEQ ID NO:16, and SEQ ID NO:17, operably linked to a heterologous nucleotide sequence encoding a polypeptide, wherein positions 1, 2, and 3 of the Kozak sequence comprise the initiating methionine codon of the polypeptide, and wherein the heterologous nucleotide sequence encoding a polypeptide is codon optimized for expression in an algal or heterokont species.

2. The recombinant DNA molecule according to claim 1, wherein the Kozak sequence is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:18, SEQ ID NO:19, and SEQ ID NO:20.

3. An expression cassette comprising the recombinant DNA molecule comprising a Kozak sequence according to claim 1, wherein the Kozak sequence is further operably linked to a eukaryotic promoter positioned upstream of the Kozak sequence.

4. The expression cassette according to claim 3, wherein the eukaryotic promoter is active in a heterokont species or a eukaryotic microalgal species.

5. The expression cassette according to claim 3, wherein the eukaryotic promoter is a Simian vacuolating virus (SV40) promoter, a cauliflower mosaic virus (CaMV) promoter, a cytomegalovirus (CMV) promoter, a promoter derived from a heterokont species, or a promoter derived from a eukaryotic microalgal species.

6. The expression cassette according to claim 5, wherein the eukaryotic promoter is a *Nannochloropsis* promoter.

7. A vector comprising an expression cassette according to claim 3.

8. The vector according to claim 7, further comprising a selectable marker.

9. A method for transforming a eukaryotic cell comprising: introducing a vector according to claim 8 into the eukaryotic cell; and
selecting for a transformed eukaryotic cell.

10. A recombinant eukaryotic microorganism comprising: a recombinant DNA molecule according to claim 1, wherein the recombinant eukaryotic microorganism produces a greater amount of the polypeptide than a control eukaryotic microorganism that is substantially identical to the recombinant eukaryotic microorganism in all respects except that the control eukaryotic microorganism comprises a recombinant DNA molecule that does not include a heterologous Kozak sequence selected from the group consisting of SEQ ID NO:13 and SEQ ID NO:14.

11. The recombinant eukaryotic microorganism according to claim 10, wherein the eukaryotic microorganism is selected from the group consisting of a fungal cell, a heterokont cell, an algal cell, and a plant cell.

12. The recombinant eukaryotic microorganism according to claim 11, wherein the eukaryotic microorganism is an algal cell.

13. The recombinant eukaryotic microorganism according to claim 12, wherein the algal cell is a species of genera selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetraselmis, Thalassiosira, Tribonema, Vaucheria, Viridiella, Vischeria,* and *Volvox.*

14. The recombinant eukaryotic microorganism according to claim 13, wherein the algal cell is a *Nannochloropsis* algal cell.

15. A method for expressing a protein of interest in a eukaryotic cell, the method comprising transfecting the eukaryotic cell with a vector comprising the expression cassette of claim 4, and culturing the eukaryotic cell under conditions in which the nucleotide sequence encoding the polypeptide is expressed.

16. The method according to claim 15, wherein the eukaryotic cell is selected from the group consisting of a fungal cell, a heterokont cell, an algal cell, and a plant cell.

17. The method according to claim 16, wherein the eukaryotic cell is an algal cell.

18. The method according to claim 17, wherein the algal cell is a species of genera selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetraselmis, Thalassiosira, Tribonema, Vaucheria, Viridiella, Vischeria,* and *Volvox*.

19. The method according to claim 18, wherein the algal cell is a *Nannochloropsis* algal cell.

20. The method according to claim 15, wherein the protein of interest is (a) a protein associated with lipid biosynthesis, (b) a protein having lipolytic activity, (c) a protein that participates in photosynthesis, (d) a protein associated with carbon fixation, (e) a transporter protein, (f) a dehydrogenase, (g) a transcription factor or (h) a cell signaling protein.

21. The method according to claim 15, wherein expression of the protein of interest is enhanced in the eukaryotic cell at least 5% relative to expression achieved from a control cell lacking the vector comprising the expression cassette of claim 4, wherein the control cell is otherwise identical to the eukaryotic cell.

22. The method according to claim 21, wherein expression of the protein of interest is enhanced in the eukaryotic cell at least 10% relative to expression achieved from the control cell.

23. The method according to claim 22, wherein expression of the protein of interest is enhanced in the eukaryotic cell at least 20% relative to expression achieved from the control cell.

* * * * *